US010807095B2

(12) United States Patent
Chou et al.

(10) Patent No.: US 10,807,095 B2
(45) Date of Patent: Oct. 20, 2020

(54) MAKING AND TRACKING ASSAY CARD

(71) Applicant: Essenlix Corporation, Monmouth Junction, NJ (US)

(72) Inventors: Stephen Y. Chou, Princeton, NJ (US); Wei Ding, East Windsor, NJ (US)

(73) Assignee: ESSENLIX CORPORATION, Monmouth Junction, NJ (US)

( * ) Notice: Subject to any disclaimer, the term of this patent is extended or adjusted under 35 U.S.C. 154(b) by 0 days.

(21) Appl. No.: 16/172,604

(22) Filed: Oct. 26, 2018

(65) Prior Publication Data
US 2019/0329260 A1 Oct. 31, 2019

Related U.S. Application Data

(60) Provisional application No. 62/577,358, filed on Oct. 26, 2017.

(51) Int. Cl.
| *B01L 3/00* | (2006.01) |
| *B01L 9/00* | (2006.01) |
| *G06K 7/14* | (2006.01) |
| *G06N 20/00* | (2019.01) |
| *G16H 10/40* | (2018.01) |
| *G06K 9/78* | (2006.01) |

(52) U.S. Cl.
CPC ............. *B01L 3/54* (2013.01); *B01L 3/50* (2013.01); *B01L 9/52* (2013.01); *G06K 7/1413* (2013.01); *G06K 7/1417* (2013.01); *G06N 20/00* (2019.01); *G16H 10/40* (2018.01); *B01L 2200/14* (2013.01); *B01L 2300/021* (2013.01); *B01L 2300/0816* (2013.01); *G06K 9/78* (2013.01); *G06K 2209/01* (2013.01)

(58) Field of Classification Search
None
See application file for complete search history.

(56) References Cited

U.S. PATENT DOCUMENTS

| 3,368,872 A | 2/1968 | Natelson |
| 3,447,863 A | 6/1969 | Patterson |
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |

(Continued)

FOREIGN PATENT DOCUMENTS

| AU | 198813789 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015.

(Continued)

*Primary Examiner* — Kristy A Haupt

(57) ABSTRACT

Among other things, the present invention is related to devices, systems, and methods of performing biological and chemical assays for certain analysis and to the identification, tracking, and monitoring of these devices and systems.

20 Claims, 4 Drawing Sheets

(56) References Cited

U.S. PATENT DOCUMENTS

| | | |
|---|---|---|
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,083,761 A | 7/2000 | Kedar et al. |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,799,558 B1 | 9/2010 | Dultz |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,144,504 B2 | 3/2012 | Kim et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,005,901 B2 | 4/2015 | Gayda et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |

(56) References Cited

U.S. PATENT DOCUMENTS

| | | |
|---|---|---|
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0180685 A1 | 7/2008 | de Laga et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2016/0350914 A1 | 12/2016 | Champlin et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 2848196 | 3/2015 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017027643 | 2/2017 |
| WO | 2017048871 | 3/2017 |
| WO | 2017048881 | 3/2017 |

OTHER PUBLICATIONS

Jahanmehr, S A H et al., Simple technique for fluorescence staining of blood cells with acridine orange, Technical Methods, Feb. 12, 1987.

Sun, Wei et al., Rapid antimicrobial susceptibility test for identification of new therapeutics and drug combinations against multidrug-resistant bacteria, Emerg. Microbes Infect., Nov. 9, 2016.

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

Written Opinion for PCT/US2018/017713 established by ISA/KR, dated Jun. 20, 2018.

A

B

C

D

MAKING AND TRACKING ASSAY CARD

CROSS REFERENCING

This application claims the benefit of U.S. Provisional Application No. 62/577,358, filed on Oct. 26, 2017, the disclosure of which is incorporated herein in its entirety for all purposes.

FIELD

Among other things, the present invention is related to devices, systems, and methods of performing biological and chemical assays for certain analysis and to the identification, tracking, and monitoring of these devices and systems.

BACKGROUND

In biological and chemical assays, it is desirable to monitor and/or track the devices for conducting these assays, such that each device can be uniquely identified for the purposes of providing or extracting information associated with the device. For instance, in some cases, it may be necessary to provide information regarding the type of assays that can be conducted using a particular device, including information relating to the assay type, assay processes, assay reagent, or assay troubleshooting. In other cases, it may be important to provide information regarding the manufacturing of the device, including the manufacturing site, manufacturing date, manufacturing process, manufacturing lot, or related personnel. Therefore, the present invention provides a new and useful way for monitoring and tracking these devices.

SUMMARY

A trackable device for sample analysis, comprising a first plate, a second plate, and a tracking label, wherein the plates are movable relative to each other into different configurations; and each of the plates comprises an inner surface that has a sample contact area for contacting a sample; wherein one of the configurations is an open configuration, in which the two plates are separated apart, and the sample is deposited on one or both of the plates; wherein another configuration is a closed configuration, which is configured after the sample is deposited on one or both the plates in the open configuration; wherein in the closed configuration at least part of the sample is compressed by the two plates into a layer of uniform thickness and is substantially stagnant relative to the plates, thereby allowing the sample in the layer to be imaged by a detecting apparatus that comprises a camera; and wherein the tracking label is on at least one of the plates and is configured to be readable by the detecting apparatus to provide information related to the device.

A trackable device for sample analysis, comprising a sample card, a tracking label, and a slider, wherein the sample card comprises two plates that are configured to compress a liquid sample into a layer of uniform thickness; the tracking label is positioned on the sample card and configured to be machine-readable by a detecting apparatus and provide information related to the sample card; and the slider is configured to hold the sample card when the liquid sample is compressed and feed the sample card into the detecting apparatus.

A trackable device for sample analysis, comprising a sample card, a tracking label, and a camera, wherein the sample card comprises two plates that are movable relative to each other into different configurations; the tracking label is positioned on the sample card and configured to be machine-readable; and the camera is configured to capture an image of the tracking label and the image is used to provide information related to the sample card; wherein one of the configurations is an open configuration, in which the two plates are separated apart, and a sample is deposited on one or both of the plates.

The device of any embodiment of the present disclosure, wherein the camera captures the image of the tracking label as the card passes the camera.

A method of tracking a device for sample analysis, comprising obtaining the device of any embodiment of the present disclosure; moving the plates into the closed configuration to form a card; inserting the card into a card slot, which is part of an adapter that is configured to attach to the detecting apparatus and position the plates in front of the camera; capturing at least one image of at least part of the tracking label with the camera; and extracting information related to the device based on the image.

The method of any embodiment of the present disclosure, wherein the card reaches a locked position after being inserted into the card slot.

The method of any embodiment of the present disclosure, where step (d) is conducted during step (c) and before the card reaches the locked position.

The method embodiment of any embodiment of the present disclosure, wherein step (d) is conducted after step (c).

The method of any embodiment of the present disclosure, further comprising the step of identifying the tracking label.

The method of any embodiment of the present disclosure, wherein the identifying step is performed during the inserting of the card into the slot, or during the removal of the card from the slot, or both.

A method of identifying a tracking label, comprising the steps of obtaining the device of any embodiment of the present disclosure; imaging the tracking label to obtain images; and analyzing the images by artificial intelligence or machine learning.

A device for identifying a tracking label, comprising the device of any embodiment of the present disclosure; an imager configured to image the tracking label to obtain images; and an algorithm configured to analyze the images by artificial intelligence or machine learning.

The device or method of any embodiment of the present disclosure, wherein the tracking label is a barcode.

The device or method of any embodiment of the present disclosure, wherein the tracking label is a 1-D barcode.

The device or method of any embodiment of the present disclosure, wherein the tracking label is a 2-D barcode.

The device or method of any embodiment of the present disclosure, wherein the tracking label is a watermark.

The device or method of any embodiment of the present disclosure, wherein the tracking label is a waveform.

The device or method of any embodiment of the present disclosure, wherein the tracking label is a machine readable medium.

The device or method of any embodiment of the present disclosure, wherein the tracking label is an image showing a string of words or numbers configured to be recognized by optional character recognition (OCR).

The device or method of any embodiment of the present disclosure, wherein the tracking label is a pattern showing a string of words or numbers configured to be recognized by optional character recognition (OCR).

The device or method of any embodiment of the present disclosure, wherein the tracking label is a periodic pattern.

The device or method of any embodiment of the present disclosure, wherein the tracking label is positioned in an inserting area on the card, wherein the inserting area is an area on the card, from a top view, that is in front of the field of view (FoV) and can be viewed through the camera and of which images can be captured if the camera is turned on during the inserting process.

The device or method of any embodiment of the present disclosure, wherein the tracking label is positioned in an overshoot area on the card, wherein the overshoot area is an area on the card, from a top view, that is on the back of the field of view (FoV) and can be viewed through the camera and of which images can be captured if the camera is turned on during the inserting process.

The device or method of any embodiment of the present disclosure, wherein the tracking label is positioned in the same area as the field of view (FOV).

The device or method of embodiment of the present disclosure, wherein the tracking label is imaged by different imagers.

The device or method of embodiment of the present disclosure, wherein the imagers have a different focal plane.

The device or method of any embodiment of the present disclosure, wherein the tracking label is positioned between the first plate and the second plate.

The device or method of any embodiment of the present disclosure, wherein the tracking label is positioned on the inner surface of the first plate.

The device or method of any embodiment of the present disclosure, wherein the tracking label is positioned on the outer surface of the first plate.

The device or method of any embodiment of the present disclosure, wherein the tracking label is positioned on the inner surface of the second plate.

The device or method of any embodiment of the present disclosure, wherein the tracking label is positioned on the outer surface of the second plate.

The device or method of any embodiment of the present disclosure, wherein the information comprises a unique identifier of the device.

The device or method of any embodiment of the present disclosure, wherein the information comprises information regarding assays that can be conducted with the device, including assay type, assay processes, assay reagent, or assay troubleshooting.

The device or method of any embodiment of the present disclosure, wherein the information comprises information regarding manufacturing of the device, including manufacturing site, manufacturing date, manufacturing process, manufacturing lot, or related personnel.

The device or method of any embodiment of the present disclosure, wherein the information comprises information regarding warranties associated with the device.

The device or method of any embodiment of the present disclosure, wherein the tracking label is produced by printing with ink.

The device or method of any embodiment of the present disclosure, wherein the tracking label is produced by engraving with light (e.g. laser).

The device or method of any embodiment of the present disclosure, wherein the tracking label is produced by a charged beam (electron or ion).

The device or method of any embodiment of the present disclosure, wherein the tracking label is produced by a nanoparticle beam.

The device or method of any embodiment of the present disclosure, wherein the tracking label is produced by etching.

The device or method of any embodiment of the present disclosure, wherein the tracking label is produced by deposition of materials.

The device or method of any embodiment of the present disclosure, wherein the lateral linear dimension of the tracking label is 0.1 µm to 1000 mm.

The device or method of any embodiment of the present disclosure, wherein the area of the tracking label is 0.01 µm$^2$ to 10,000 mm$^2$.

The device or method of any embodiment of the present disclosure, further comprising spacers affixed on one or both of the plates.

The device or method of any embodiment of the present disclosure, wherein at least part of the spacers are used as the tracking label.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Among other things, the present invention provides devices, systems, and methods of performing biological and chemical assays using a QMAX card.

QMAX Card

Figure 1:
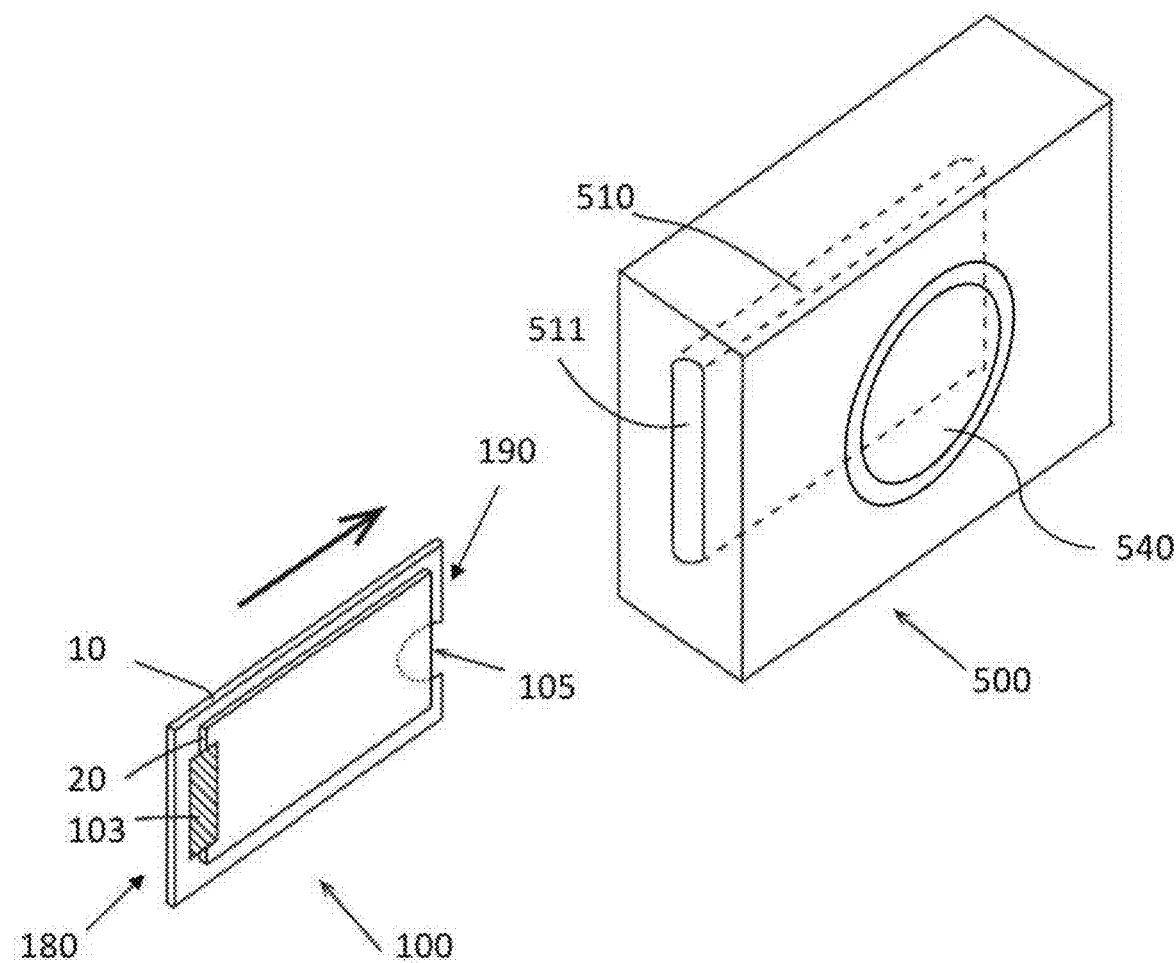
FIG. 1 shows an exemplary embodiment of the QMAX (Q: quantification; M: magnifying; A: adding reagents; X: acceleration; also known as compressed regulated open flow (CROF)) card and a simplified illustration of an adapter that is configured to accommodate the QMAX card and measure the sample in the QMAX card, which comprises a first plate and a second plate connected by a hinge. The QMAX card can be inserted into a slot of the adapter, which can be attached to a mobile communication device (e.g. a smart phone) that comprises a camera and a light source. The mobile communication device can be used to capture images of a sample in the QMAX card and analyze the images to measure and/or detect specific analytes for various purposes. The adapter comprises a camera viewing outlet, which is the structure that optically connects to the camera, allowing the camera to capture images of the sample in the QMAX card.

The current invention relates to identifying, tracking, and/or monitoring of any device that can be imaged for certain analysis (e.g. bio/chemical assays). FIG. 1 shows an exemplary embodiment of the QMAX (Q: quantification; M: magnifying; A: adding reagents; X: acceleration; also known as compressed regulated open flow (CROF)) card 100 and a simplified illustration of an adapter 500. As shown in FIG. 1, in some embodiments, the QMAX card comprises a first plate 10, a second plate 20, and a hinge 103 that connects the first plate 10 and the second plate 20 so that the two plates can pivot against each other. In some embodiments, one or both of the plates are transparent. In some embodiments, one or both of the plates are flexible.

In some embodiments, the plates are movable relative to each other into different configurations. One of the plate configurations is an open configuration, wherein the two plates are least partially separated apart, allowing a liquid sample to be deposited on one or both of the plates. Another configuration is a closed configuration, wherein at least part of the sample deposited in the open configuration is compressed by the two plates into a layer of highly uniform thickness, the uniform thickness of the layer is confined by the inner surfaces of the plates and is stagnant relative to the plates. In certain embodiments, the average spacing between the plates is larger than 300 um; in certain embodiments, the average spacing between the plates is 200 um or less.

In some embodiments, the QMAX card further comprises spacers (not shown in FIG. 1) that can regulate the spacing between the first plate 10 and the second plate 20. In certain embodiments, the spacers are pillar structures that are fixed on one or both of the plates. When the plates are in the open configuration, the spacing between the plates is not regulated by the spacers; when the plates are in the closed configuration, the spacing between the plates are regulated by the spacers. In some embodiments, the spacers 40 have a predetermined uniform height and a predetermined uniform inter-spacer distance. In certain embodiments, in the closed configuration the spacing between the plates is substantially the same as the height of the spacers; accordingly, in certain embodiments, the thickness of the sample layer is substantially the same as the spacing between the plates and the height of the spacers.

In some embodiments, the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values. In certain embodiments, at least one of the plates is in the range of 0.5 to 1.5 mm; around 1 mm; in the range of 0.15 to 0.2 mm; or around 0.175 mm.

In some embodiments, at least one of the plate is 1 $mm^2$ (square millimeter) or less, 10 $mm^2$ or less, 25 $mm^2$ or less, 50 $mm^2$ or less, 75 $mm^2$ or less, 1 $mm^2$ (square centimeter) or less, 2 $mm^2$ or less, 3 $mm^2$ or less, 4 $mm^2$ or less, 5 $mm^2$ or less, 10 $mm^2$ or less, 100 $mm^2$ or less, 500 $mm^2$ or less, 1000 $mm^2$ or less, 5000 $mm^2$ or less, 10,000 $mm^2$ or less, 10,000 $mm^2$ or less, or in a range between any two of these values. In certain embodiments, at least one plate of the QMAX card is in the range of 500 to 1000 $mm^2$; or around 750 $mm^2$.

In some embodiments, the lateral linear dimension (width, length, or diameter, etc) of at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values. In certain embodiments, the lateral linear dimension of at least one plate of the QMAX card is in the range of 20 to 30 mm; or around 24 mm.

Figure 3:
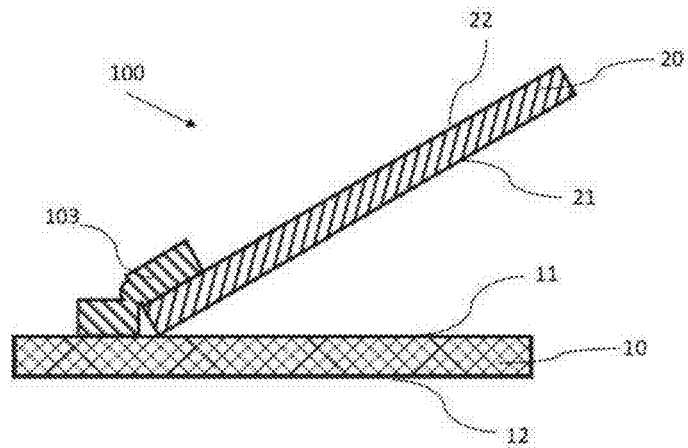
FIG. 3 shows a sectional view of the QMAX card in an open configuration, illustrating outer and inner surfaces of the QMAX card.

In some embodiments, the QMAX card comprises a hinge 103 (also referring to FIG. 3), which connect the first plate 10 and the second plate 20 and allow the plates to pivot against each other. In such a manner, the plates can be switched between the open configuration and the closed configuration. FIG. 1 shows the QMAX card in the closed configuration; FIG. 3 shows the QMAX card in the open configuration.

In some embodiments, the QMAX comprises a notch 105, which facilitates the switching of the card between the open configuration and the closed configuration. In certain embodiments, the notch 105 is on one plate (e.g. the first plate 10) while a corresponding edge of the other plate (e.g. the second plate 20) is positioned over it to allow a user to push against the edge to open or close the QMAX card.

The adapter 500 is configured to accommodate the QMAX card 100 and measure the sample in the QMAX card. As shown in FIG. 1, the QMAX card 100, in the closed configuration, can be inserted into a card slot 510 of the adapter 500, which can be attached to a detection apparatus that can be used to measure and/or detect one or more analytes in the sample in the QMAX card. As a whole, the QMAX card has a front end 190 and a back end 180, which are defined by the direction (referring to the arrow in FIG. 1) in which the card 100 is inserted into the slot 510. The front end 190 is the first end of the QMAX card 100 that passes through the slot opening 511; the back end 180 is opposite to the front end 190.

In some embodiments, the detection apparatus 500 is a mobile communication device (e.g. a smart phone) that comprises a camera and a light source. The camera of the mobile communication device can be used to capture images of a sample in the QMAX card and analyze the images to measure and/or detect specific analytes in the sample for various purposes. In some embodiments, the adapter 500 comprises a camera viewing outlet 540, which is the structure that optically connects to the camera in the detection apparatus, allowing the camera to capture images of the sample in the QMAX card 100.

Tracking Label and Label Types

Figure 2:
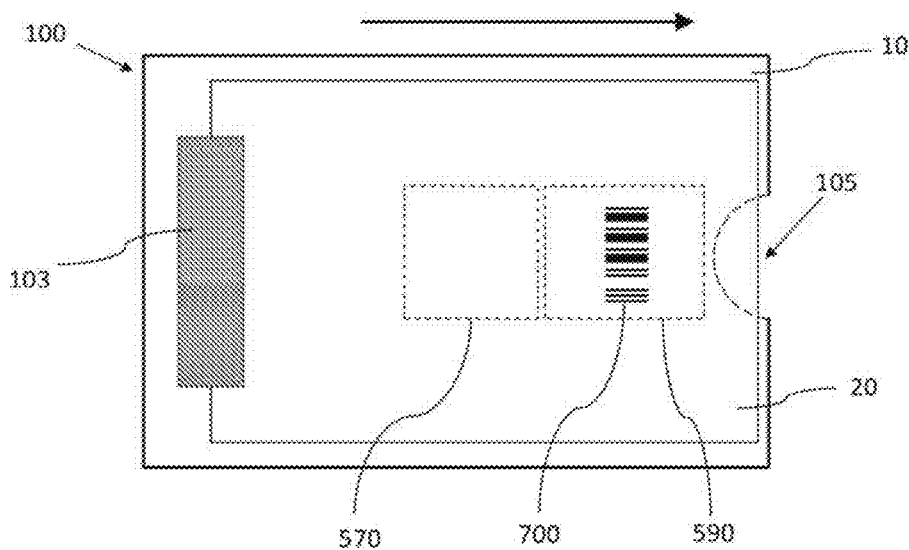
FIG. 2 shows top views of the QMAX card embodiments with tracking labels according to some embodiments of the present invention. After the inserting into the adapter, the QMAX card can settle into a locked position and part of the card is under a combination of lens(es) in the adapter and lens(es) of the camera, which define a field of view (FoV) on the QMAX card. Panel (A) shows the top view of the QMAX card, illustrating a tracking label (in the form of a 1-D barcode) positioned in an inserting area, which is in front of (as defined by the direction of insertion) the FoV in the QMAX card. The type, position, size, and printing method of the tracking label can vary. Panel (B) shows the top view of the QMAX card, illustrating a tracking label (in the form of a 1-D barcode) positioned in an overshoot area, which is to the back of (as defined by the direction of insertion) the FoV in the QMAX card.
Figure 2:
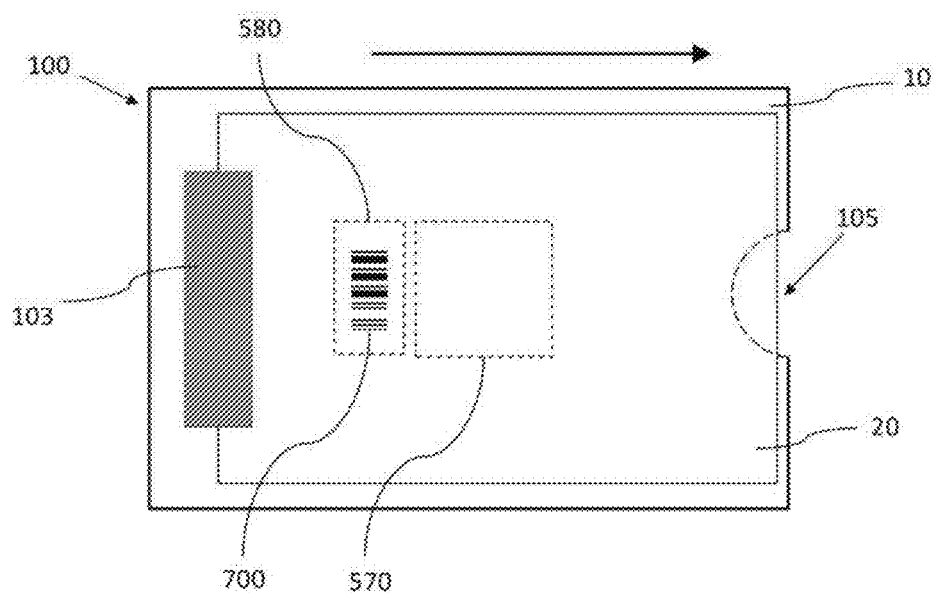

FIG. 2 shows top views of the QMAX card 100 with tracking labels 700 according to some embodiments of the present invention. In some embodiments, it is desirable to monitor and/or track the QMAX card; in some embodiments, it is desirable that each card can be uniquely identified so certain information associated with the card can be extracted. In some embodiments, a machine readable tracking label 700 can be added to the card so that the card can be tracked, identified, and/or monitored.

Figure 4:
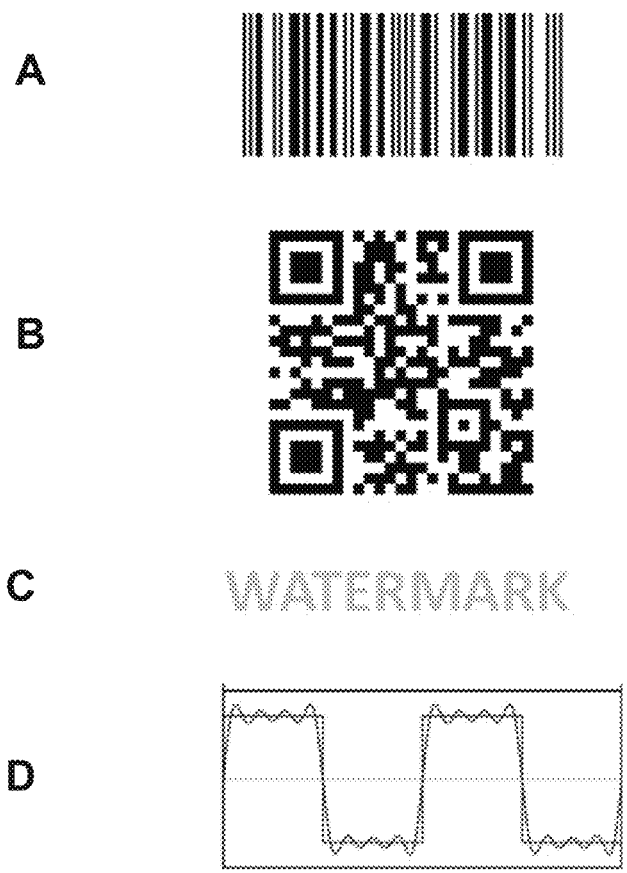
FIG. 4 shows some examples of tracking label types according to some embodiments of the current invention. Panel (A): 1-D barcode; panel (B): 2-D barcode; panel (C): watermark; panel (D): waveform. In various embodiments, the tracking label types can vary and can be combined. Other tracking label types can also be used.
Figure 5:
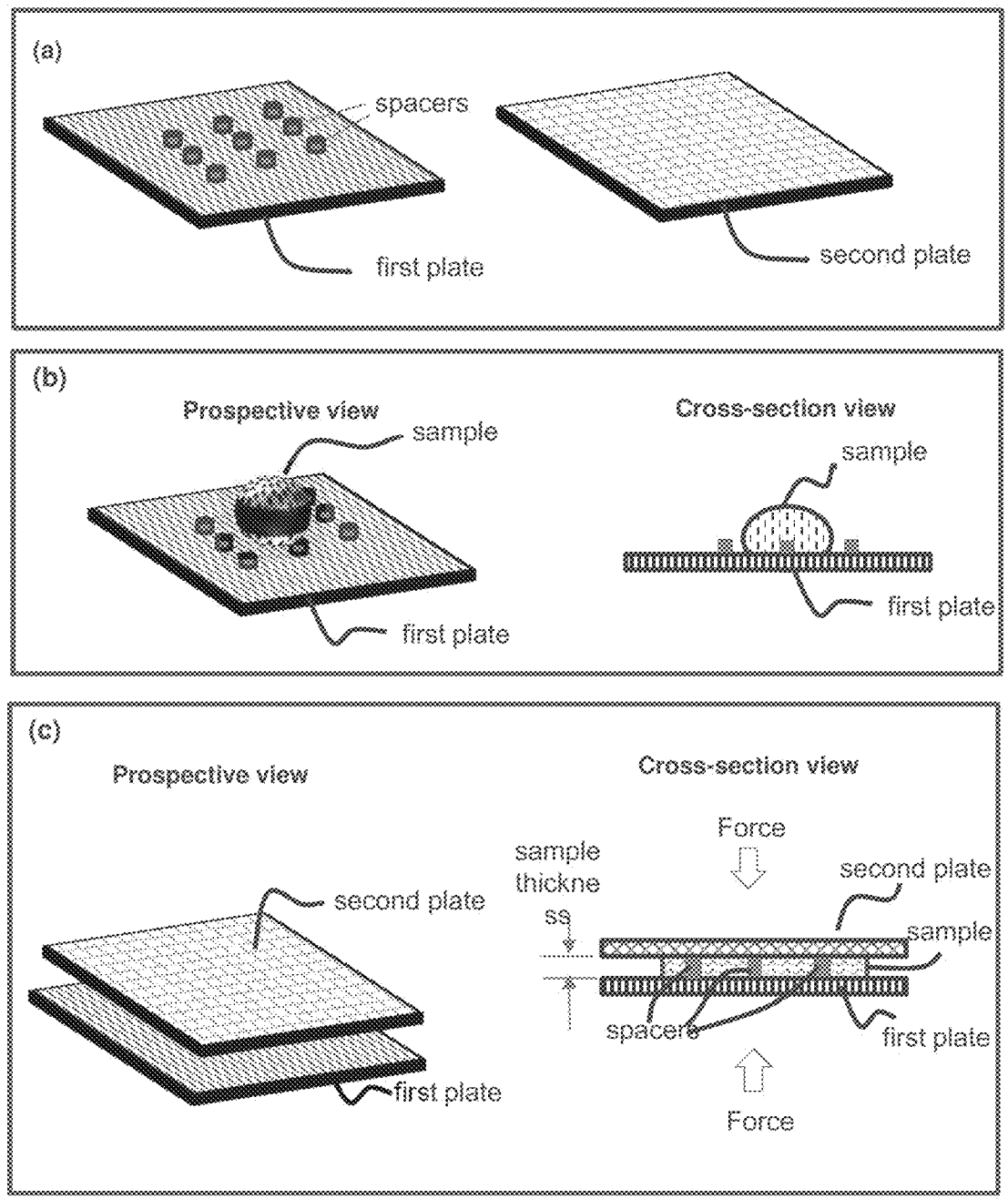
FIG. 5 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).

In essence, the tracking label 700 can be any type of code, word, image or pattern that can be machine readable and capable of uniquely identifying a device and its associated information (e.g. assay, dimension, manufacturing date, etc.). FIG. 4 shows some examples of tracking label types according to some embodiments of the current invention. Panel (A): 1-D barcode; panel (B): 2-D barcode; panel (C): watermark; panel (D): waveform. In various embodiments, the tracking label types can vary and can be combined. Other tracking label types can also be used.

As shown in panel (A) of FIG. 4, the tracking label 700 can be a 1-D barcode. The term "barcode" refers to an optical, machine readable, representation of data, which describes the device to which the barcode is attached. The term "1-D barcode" or "one dimensional" barcode refers to a barcode made up of lines and spaces of various widths that create specific patterns. For example, the barcode 700 can be a 1-D barcode that includes but is not limited to the universal product code (UPC), which consists of 12 numerical digits, the European Article Number (EAN, also known as international article number) barcode, the global trade item number barcode (GTIN). For example, in some embodiments, the 1-D barcode can be printed, molded, and/or engraved in the QMAX card.

As shown in panel (B) of FIG. 4, the tracking label 700 can be a 2-D barcode. The term "2-D barcode" or "matrix barcode" refers to a barcode that uses a two dimensional pattern to represent information. For example, the barcode 700 can be 2-D barcode that includes but is not limited to the Aztec code, the data matrix barcode, the PDF417 barcode, the Qode, the Shotcode, and the SPARQCode (QR code). For example, in some embodiments, the 2-D barcode can be printed, molded, and/or engraved in the QMAX card.

As shown in panel (C) of FIG. 4, the tracking label 700 can be a watermark. Here, the term "watermark" refers to an image or pattern that has various shades of lightness/darkness shown in an image captured by a camera, so that the image and pattern can be used to identify the device to which the water is attached and to extract information associated with the device. For example, in some embodiments, the watermark can be printed, molded, and/or engraved in the QMAX card.

As shown in panel (D) of FIG. 4, the tracking label 700 can be a waveform pattern. waveform is the shape and form of a signal such as a wave moving in a physical medium or an abstract representation. For example, in some embodiments, the waveform can be printed, molded, and/or engraved in the QMAX card. A specific waveform can be a combination of simpler waveforms, and can be imaged and the images can be used to extract information related to the device to which the waveform is attached.

It should be noted that the embodiments shown in FIG. 4 present only examples of the tracking label. For instance, the tracking label can be an image or pattern that shows a string of words and/or numbers that can be recognized by optional character recognition (OCR). In addition, the specific methods to encode information associated with the device can vary and the embodiments can be combined and/or re-arranged.

In certain embodiments, at least a part of the spacers are used as the tracking labels, wherein the tracking labels have a patterns described in the disclosure.

In certain embodiments, the tracking labels comprises periodic patterns.

Size of the Tracking Label

The tracking label 700 can be any size that is proper for the identification, monitoring, tracking, and information extraction for the QMAX card 100.

In some embodiments, the lateral linear dimension (length, width, or diameter, etc.) of the tracking label 700 is 0.1 um or less, 0.5 um or less, 1 um or less, 5 um or less, 10 um or less, 15 um or less, 20 um or less, 25 um or less, 30 um or less, 35 um or less, 40 um or less, 45 um or less, 50 um or less, 100 um or less, 200 um or less, 300 um or less, 400 um or less, 500 um or less, 750 um or less, 1 mm or less, 5 mm or less, 10 mm or less, 100 mm or less, or 1000 mm or less, or in a range between any two of these values.

In some embodiments, the lateral linear dimension (length, width, or diameter, etc.) of the FoV 570 is 0.1 um or less, 1 um or less, 10 um or less, 50 um or less, 100 um or less, 500 um or less, 1 mm or less, 10 mm or less, 100 mm or less, or 1000 mm or less, or in a range between any two of these values. In some embodiments, the ratio of the lateral linear dimension (length, width, or diameter, etc.) of the tracking label 700 to the lateral linear dimension (length, width, or diameter, etc.) of the FoV is 1/1000 or less, 1/500 or less, 1/100 or less, 1/50 or less, 1/10 or less, 1/5 or less, 1/4 or less, 1/3 or less, 1/2 or less, 2/3 or less, 3/4 or less, 1 or less, 2 or less, 3 or less, 4 or less, 5 or less, 10 or less, 50 or less, 100 or less, 200 or less, 500 or less, 1000 or less, or in a range between any two of these values.

In some embodiments, the area of the tracking label 700 is 0.01 $um^2$ or less, 0.05 $um^2$ or less, 0.1 $um^2$ or less, 0.5 $um^2$ or less, 1 $um^2$ or less, 5 $um^2$ or less, 10 $um^2$ or less, 15 $um^2$ or less, 20 $um^2$ or less, 25 $um^2$ or less, 30 $um^2$ or less, 35 $um^2$ or less, 40 $um^2$ or less, 45 $um^2$ or less, 50 $um^2$ or less, 100 $um^2$ or less, 200 $um^2$ or less, 300 $um^{22}$ or less, 400 $um^2$ or less, 500 $um^2$ or less, 750 $um^2$ or less, 1 $mm^2$ or less, 5 $mm^2$ or less, 10 $mm^2$ or less, 100 $mm^2$ or less, 1000 $mm^2$ or less, 5000 $mm^2$ or less, 10000 $mm^2$ or less, or in a range between any two of these values.

In some embodiments, the area of the tracking label 700 is 0.01 $um^2$ or less, 0.1 $um^2$ or less, 1 $um^2$ or less, 10 $um^2$ or less, 50 $um^2$ or less, 100 $um^2$ or less, 500 $um^2$ or less, 1 $mm^2$ or less, 10 $mm^2$ or less, 100 $mm^2$ or less, 1000 $mm^2$ or less, 10000 $mm^2$ or less, or in a range between any two of these values. In some embodiments, the ratio of the area of the tracking label 700 to area of the FoV is 1/1000 or less, 1/500 or less, 1/100 or less, 1/50 or less, 1/10 or less, 1/5 or less, 1/4 or less, 1/3 or less, 1/2 or less, 2/3 or less, 3/4 or less, 1 or less, 2 or less, 3 or less, 4 or less, 5 or less, 10 or less, 50 or less, 100 or less, 200 or less, 500 or less, 1000 or less, or in a range between any two of these values.

Location of the Tracking Label on the Card and Its Reading

In some embodiments, after being inserted into the adapter, the QMAX card settles into a locked position so that the sample in the QMAX card can be imaged with the camera in the detection apparatus. For example, a push-push mechanism (e.g. as described in U.S. Pat. Nos. 6,572,392 and 7,077,671, which are incorporated in their entirety for all purposes) can be used for the insertion, position-locking, and extraction of the card 100. In the locked position, the card cannot be moved relative to the adapter without specific triggering mechanism. In addition, when the card is in the locked position, at least part of the card is under a combination of lens(es) in the adapter and lens(es) of the camera. The area in the card that can be viewed and from which images can be captured is defines as the field of view (FoV) in the locked position. For instance, in FIG. 2, panels (A) and (B), the FoV is shown as 570 on the QMAX card.

Panel (A) of FIG. 2 shows the top view of the QMAX card 100, illustrating a tracking label 700 (in the form of a 1-D barcode) positioned in an inserting area 590, which is in front of (as defined by the direction of insertion, shown by the arrow in FIG. 2) the FoV in the QMAX card. Panel (B) of FIG. 2 shows the top view of the QMAX card 100, illustrating a tracking label 700 (in the form of a 1-D barcode) positioned in an overshoot area 580, which is to the back of (as defined by the direction of insertion, shown by the arrow in FIG. 2) the FoV in the QMAX card.

Various mechanisms can be employed to facilitate the insertion and locking of the QMAX card 100 in the adapter 500. When in the locked position, the area of the card can be viewed through the camera and of which images can be captured is the FoV. Here, the direction in which the card is inserted (as shown by the arrows in FIG. 2) is considered moving from the back of the FoV to the front. In some embodiments, before the card reaches the locked position, parts of the card pass before the lens of the camera, allowing the camera to capture images of the those parts. The term "inserting area" is defined as the area on the card, from a top view, that is in front of the FoV and can be viewed through the camera and of which images can be captured if the camera is turned on during the inserting process. In some embodiments, the tracking label 700 is in the inserting area of the card from a top view, disregarding where the tracking label 700 is physically lodged on which surface of which plate.

In certain embodiments, the tracking label is in the same area of the FoV of the analyte detection. In certain embodiments, the tracking label is in the same area of the FoV of the analyte detection, and the tracking label is (a) between the two plate, (b) on an inner surface of the plates, (c) on the outer surface of the plates, (d) inside of the plates, or (e) any combination of thereof.

In certain embodiments, the tracking label is in the same area of the FoV of the analyte detection, and the tracking label is imaged by different images with, in some embodiments, each image has a different focal plane.

In addition, in some embodiments of the current invention, certain inserting mechanisms involve an "overshoot" of the card, which means that the furthest position of the card in the inserting process is to the back of the locked position.

The term "overshoot area" is defined as the area on the card, from a top view, that is to the back of the FoV and can be viewed through the camera and of which images can be captured if the camera is turned on during the inserting process. In some embodiments, the tracking label 700 is in the overshoot area of the card from a top view, disregarding where the tracking label 700 is physically lodged on which surface of which plate.

It is also possible that the tracking label 700 is partly or entirely positioned within the FoV. In some embodiments, the tracking label 700 is partly or entirely in the FoV of the card from a top view, disregarding where the tracking label 700 is physically lodged on which surface of which plate. In certain embodiments, the tracking label 700 is positioned within the FoV but does not interfere with the image capturing process of the FoV. In certain embodiments, the tracking label 700 is positioned within the FoV but does not interfere with the structure of the spacers in the FoV.

FIG. 3 shows a sectional view of the QMAX card in an open configuration, illustrating outer and inner surfaces of the QMAX card. As shown in FIG. 3, the first plate 10 comprises an inner surface 11 and an outer surface 12; the second plate 20 comprises an inner surface 21 and an outer surface 22. In some embodiments, in the closed configuration, the inner surfaces 11 and 21 of the first plate 10 and the second plate 20 face each other to confine a sample (if a sample is deposited on one or both of the plates in the open configuration). In certain embodiments, the first plate 10 and the second plate 20 compress at least part of the sample into a layer of uniform thickness, which can be regulated by spacers fixed on one or both of the plates or mixed with a sample.

In some embodiments, the tracking label 700 can be physically lodged (e.g. printed, engraved, or etched) on one or more surfaces of the plates. In certain embodiments, the tracking label 700 is lodged on the inner surface 11 of the first plate 10, on the inner surface 21 of the second plate 20, on the outer surface 12 of the first plate 10, on the outer surface 22 of the second plate 20, or a combination thereof. In some embodiments, the tracking label 700 is positioned in more than one surface.

It should be noted that the vertical positioning (e.g. on which surface of which plate) of the tracking label 700 can be independently chosen from the lateral positioning (e.g. in which area from the top view). For example, in certain embodiments, the tracking label 700 is positioned on the outer surface 12 or 22 (of the first plate 10 or second plate 20) and in the FoV, thus the tracking label 700 does not interfere with the structure between the inner surfaces 11 and 21 (so not in touch with sample).

In certain embodiments, the identification of a tracking label comprising (a) imaging of the tracking label and (b) analyzing the images by artificial intelligence and/or machine learning.

In certain embodiments, the device for identification of a tracking label comprising (a) an imager for imaging the tracking label and (b) a device that contains an algorithm that analyze the images by artificial intelligence and/or machine learning.

In certain embodiments, the tracking label is identified by being imaged during the a process of the QMAX card being inserted or removed or both. One advantage of such process is that a tracking label that is not in FoV of a camera when the sample is in a locked position can be viewed by the same camera.

Printing Methods

The tracking label 700 can be lodged to the plates in any way possible, as long as the reading of the label and analysis of the sample can be carried out. In some embodiments, the tracking label 700 is lodged on a separate structure (e.g. a piece of paper, glass, plastic) and that structure is attached to the plates at a specific position. In some embodiments, the tracking label 700 is directly lodged on one or both of the plates.

In some embodiments, the tracking label 700 is printed on a separate structure or on one or both of the plates directly. For instance, in certain embodiments, the tracking label 700 is produced with inkjet printing or laser printing, or both. In some embodiments, the tracking label 700 is engraved on a separate structure or one or both of the plates directly. For instance, in certain embodiments, the tracking label 700 is engraved by light (e.g. laser), by charged beam (electron or ion), or by nanoparticle beam, or by a combination of the same. In some embodiments, the tracking label 700 is lodged on a separate structure or one or both of the plates directly by etching. In some embodiments, the tracking label 700 is lodged on a separate structure or one or both of the plates directly by deposition of materials. In some embodiments, the tracking label 700 is lodged on a separate structure or one or both of the plates directly by a combination of methods.

Methods to Capture Image and Reading the Tracking Label

In some embodiments, when the card 100 is being inserted into the card slot 510 and before the card 100 settles in the locked position, a number of areas pass before the lenses of the camera and/or the adapter. In certain embodiments, the camera captures at least an image of the tracking label 700, which positioned in the inserting area 590, the FoV 570, or the overshoot area 580, or partly in one area and partly in another. In certain embodiments, the camera is turned on before the insertion of the card 100 and captures at least an image of the tracking label 700 during the insertion process (before the card 100 reaches the locked position). In certain embodiments, the camera is turned on during the insertion of the card 100 (e.g. by automatically detecting the insertion of the card) and captures at least an image of the tracking label 700 after being turned on. In certain embodiments, the camera captures at least an image of the tracking label 700 when the card 100 is in the locked position.

In certain embodiments, when the tracking label 700 is positioned within the FoV, the camera captures at least an image which includes part of all of the tracking label 700 as well as part or all of the sample in the FoV. In certain embodiments, the capturing of the tracking label 700 and the sample in the same image facilitates analysis of the image/sample and/or tracking of the sample/device. In certain embodiments, the camera is kept on before the card 100 is extracted from the card slot and captures at least an image of the tracking label 700 after the card 100 is moved from the locked position and before the card is taken out of the card slot, wherein the tracking label 700 is positioned in the inserting area 590, the FoV 570, or the overshoot area 580, or partly in one area and partly in another.

In some embodiments, after the image that includes at least part the tracking label is captured, information that is related to the device can be extracted. In such a manner, the device and/or the sample in the device can be identified, tracked, and/or monitored. The images can be analyzed by a computing unit, which can be any device or part of a device that possesses computing, communication, and/or data storage capabilities. In certain embodiments, the computing unit is part of the detection apparatus. In certain embodiments, the computing unit is part of a mobile communication device, e.g. a smart phone. After the information is extracted, the information, or part of the information, can be sent to another device (e.g. a remote server) or displayed by another device or on the detection apparatus.

Artificial Intelligence and/or Machine Learning to Improve Imaging and Mark Identification.

In certain embodiments of the present invention, the images taken during an assay operation and/or the samples measured by an assay are analyzed by artificial intelligence and machine learning. The samples include, but not limited to, medical samples, biology samples, environmental samples and chemistry samples.

In certain embodiments of the present invention, the sample is held by a QMAX device. The QMAX device together with imaging plus artificial intelligence and/or machine learning can overcome certain limitations in prior arts.

One important aspect of the present invention is to provide a machine learning framework to enhance the functionality, application scope and the accuracy in assaying using QMAX device, especially when a computer program is used.

In certain embodiments of the present invention, a device and a method for assaying sample and/or assay operation (e.g. tracking label identification) that utilizes QMAX together with imaging plus a machine learning and/or artificial intelligence comprises:

(1) using a QMAX device that has an auxiliary structure in the form of pillars to precisely control the distribution and volume of the sample in assaying, wherein the sample for assaying is loaded into the QMAX device and is kept between the two parallel plates on the QMAX device with an upper plate being transparent for imaging by an imager;

(2) the gap between the two parallel plates in the QMAX device is spaced narrowly—with the distance of the gap being proportional to the size of the analytes to be assayed—by which the analytes in the sample form a single layer between the said plates that can be imaged by an imager on the QMAX device;

(3) the sample volume corresponding to the AoI (area-of-interest) on the upper plate of the QMAX device can be precisely characterized by AoI and the gap—because of the uniformity of the gap between the plates in the QMAX device;

(4) the image on the sample for assaying sandwiched between the AoI x gap in the QMAX device is a pseudo-2D image, because it has the appearance of a 2D image, but it is an image of a 3D sample with its depth being known priori or characterized through other means;

(5) the captured pseudo-2D sample image taken over the AoI of the QMAX device can characterize the location of the analytes, color, shape, counts, and concentration of the analytes in the sample for assaying;

(6) based on abovementioned properties, the captured pseudo-2D image of QMAX device for assaying is amendable to a machine learning framework that applies to analyte detection, localization, identification, segmentation, counting, etc. for assaying in various applications; or (7) any combination of thereof.

In certain embodiments of the present invention, a machine learning framework for QMAX based devices are implemented into a device that is capable of running an algorithms such as deep learning to discriminatively locate, identify, segment and count analytes (e.g. blood cells) based on the pseudo-2D image captured by the QMAX imager.

In certain embodiments of the present invention, the machine learning improves the images captured by the imager on the QMAX device and reduces the effects of noise and artifacts—including and not limited to air bobbles, dusts, shadows, and pillars.

In certain embodiments of the present invention, the training of machine learning uses the spacers of the QMAX card to reduce the data size of training set.

Information Associated with the Card

Various types of information can be extracted from the tracking label 700. In some embodiments, the information is a code or digital string that identify the device. In certain embodiments, the code or digital string can be used to uniquely identify the device carrying the tracking label.

In some embodiments, the information that can be extracted from the image or the tracking label 700 also includes, for example, information related to the sample that is collected. For example, in certain embodiments, part or all of the tracking label corresponds to the type of the sample, e.g. blood sample, saliva sample, etc. In certain embodiments, part or all of the tracking label corresponds to the provider of the sample, e.g. specific individual or certain types of individuals (e.g. cancer patients).

In some embodiments, the information that can be extracted from the image or the tracking label 700 also includes, for example, information related to the assay that is to be conducted (or have been conducted) with the device. For example, in certain embodiments, part or all of the tracking label corresponds to the type of the assay, e.g. blood glucose assay, chemical binding assay, biomarker assay, environmental marker assay, etc. In certain embodiments, part or all of the tracking label corresponds to the person that conducts the assay, e.g. specific individual or certain types of individuals (e.g. medical professionals or layman users).

In some embodiments, the information that can be extracted from the image or the tracking label 700 also includes, for example, information related to the manufacturing of the device. For example, in certain embodiments, part or all of the tracking label corresponds to the manufacturing lot number of the device. In certain embodiments, part or all of the tracking label corresponds to the manufacturing date of the device. In certain embodiments, part or all of the tracking label corresponds to the manufacturing site of the device.

EXAMPLES OF PRESENT INVENTION

A1. A trackable device for sample analysis, comprising:
a first plate, a second plate, and tracking label, wherein:
i. the plates are movable relative to each other into different configurations;
ii. each of the plates comprises an inner surface that has a sample contact area for contacting a sample; and
iii. a tracking label;
wherein one of the configurations is an open configuration, in which the two plates are separated apart, and the sample is deposited on one or both of the plates;
wherein another configuration is a closed configuration which is configured after the sample deposition in the open configuration: at least part of the sample is compressed by the two plates into a layer of highly uniform thickness and is substantially stagnant relative to the plates, allowing the sample in the layer to be imaged by a detecting apparatus that comprises a camera; and
wherein the tracking label is on at least one of the plates, and is configured to be readable by the detecting apparatus to provide information related to the device.

A2. A trackable device for sample analysis, comprising:
a sample card, a tracking label, and slider, wherein:
i. the sample card comprises two plates that are configured to compress a liquid sample into a layer of uniform thickness;
ii. the tracking label that is positioned on the sample card and configured to be machine-readable by a detecting apparatus and provide information related to the sample card; and
iii. the slider that is configured to hold the sample card when the liquid sample is compressed and feed the sample card into the detecting apparatus.

A3. A trackable device for sample analysis, comprising:
a sample card, a tracking label, and a camera, wherein:
i. the sample card comprises two plates that are movable related to each other into different configurations;
ii. the tracking label that is positioned on the sample card and configured to be machine-readable; and
iii. the camera is configured to capture an image of the tracking label and the image is used to provide information related to the sample card;
wherein one of the configurations is an open configuration, in which the two plates are separated apart, and a sample is deposited on one or both of the plates;

A4. The trackable device or embodiment A3, wherein the camera captures the image of the tracking label as the card passes the camera.

B1. A method to track a device for sample analysis, comprising:
(a) obtaining the device of embodiment A1;
(b) switching the plates into the closed configuration to form a card;
(c) inserting the card into a card slot, which is part of an adapter that is configured to attach to the detecting apparatus and position the plates in front of the camera;
(d) capturing at least one image of at least part of the tracking label with the camera; and
(e) extracting information related to the device based on the image.

B2. The method of embodiment B1, wherein the card reaches a locked position after being inserted into the card slot.

B3. The method of any prior method embodiment, where step (d) is conducted during step (c) and before the card reaches the locked position.

B4. The method of any prior method embodiment, wherein step (d) is conducted after step (c).

Tracking Label Type

C1. The device or method of any prior embodiments, wherein the tracking label is a barcode.

C2. The device or method of any prior embodiments, wherein the tracking label is a 1-D barcode.

C3. The device or method of any prior embodiments, wherein the tracking label is a 2-D barcode, including but not limited to the Aztec code, the data matrix barcode, the PDF417 barcode, the Qode, the Shotcode, and the SPARQCode (QR code).

C4. The device or method of any prior embodiments, wherein the tracking label is a watermark.

C5. The device or method of any prior embodiments, wherein the tracking label is a waveform.

C6. The device or method of any prior embodiments, wherein the tracking label is machine readable medium.

C7. The device or method of any prior embodiments, wherein the tracking label is a printed radio frequency identification circuit.

Tracking Label Position

D1. The device or method of any prior embodiments, wherein the tracking label is positioned in an inserting area on the card, wherein the inserting area is an area on the card, from a top view, that is in front of the field of view (FoV) and can be viewed through the camera and of which images can be captured if the camera is turned on during the inserting process.

D2. The device or method of any prior embodiments, wherein the tracking label is positioned in an overshoot area on the card, wherein the overshoot area is an area on the card, from a top view, that is on the back of the field of view (FoV) and can be viewed through the camera and of which images can be captured if the camera is turned on during the inserting process.

D3. The device or method of any prior embodiments, wherein the tracking label of positioned on the inner surface of the first plate.

D4. The device or method of any prior embodiments, wherein the tracking label of positioned on the outer surface of the first plate.

D5. The device or method of any prior embodiments, wherein the tracking label of positioned on the inner surface of the second plate.

D6. The device or method of any prior embodiments, wherein the tracking label of positioned on the outer surface of the second plate.

D7. The device or method of any prior embodiments, wherein the tracking label is printed radio frequency identification circuit and the position of the tracking label is detected by the near field communication (NFC) module of the camera.

Information

E1. The device or method of any prior embodiments, wherein the information comprises a unique identifier of the device.

E2. The device or method of any prior embodiments, wherein the information comprises information regarding assays that can be conducted with the device, including assay type, assay processes, assay reagent, and/or assay troubleshooting.

E3. The device or method of any prior embodiments, wherein the information comprises information regarding manufacturing of the device, including manufacturing site, manufacturing date, manufacturing process, manufacturing lot, and/or related personnel.

E4. The device or method of any prior embodiments, wherein the information comprises information regarding warranties associated with the device.

Tracking Label Production

F1. The device or method of any prior embodiments, wherein the tracking label is produced by printing with ink.

F2. The device or method of any prior embodiments, wherein the tracking label is produced by engraving with light (e.g. laser), F3. The device or method of any prior embodiments, wherein the tracking label is produced by charged beam (electron or ion)

F4. The device or method of any prior embodiments, wherein the tracking label is produced by nanoparticle beam, F5. The device or method of any prior embodiments, wherein the tracking label is produced by etching, F6. The device or method of any prior embodiments, wherein the tracking label is produced by deposition of materials.

F7. The device or method of any prior embodiments, wherein the tracking label is produced by printing with fluorescent ink which is not visible unless exposed under illumination of light of specific wavelength.

F8. The device or method of any prior embodiments, wherein the tracking label is produced by printing with conductive ink.

F9. The device or method of any prior embodiments, wherein the tracking label is produced by printing with magnetic ink.

Tracking Label Size

G1. The device or method of any prior embodiments, wherein the lateral linear dimension (length, width, or diameter, etc.) of the FoV is 0.1 um or less, 1 um or less, 10 um or less, 50 um or less, 100 um or less, 500 um or less, 1 mm or less, 10 mm or less, 100 mm or less, or 1000 mm or less, or in a range between any two of these values.

G2. The device or method of any prior embodiments, wherein the ratio of the lateral linear dimension (length, width, or diameter, etc.) of the tracking label to the lateral linear dimension (length, width, or diameter, etc.) of the FoV is 1/1000 or less, 1/500 or less, 1/100 or less, 1/50 or less, 1/10 or less, 1/5 or less, 1/4 or less, 1/3 or less, 1/2 or less, 2/3 or less, 3/4 or less, 1 or less, 2 or less, 3 or less, 4 or less, 5 or less, 10 or less, 50 or less, 100 or less, 200 or less, 500 or less, 1000 or less, or in a range between any two of these values.

G3. The device or method of any prior embodiments, wherein the area of the tracking label is 0.01 um2 or less, 0.05 um2 or less, 0.1 um2 or less, 0.5 um2 or less, 1 um2 or less, 5 um2 or less, 10 um2 or less, 15 um2 or less, 20 um2 or less, 25 um2 or less, 30 um2 or less, 35 um2 or less, 40 um2 or less, 45 um2 or less, 50 um2 or less, 100 um2 or less, 200 um2 or less, 300 um22 or less, 400 um2 or less, 500 um2 or less, 750 um2 or less, 1 mm2 or less, 5 mm2 or less, 10 mm2 or less, 100 mm2 or less, 1000 mm2 or less, 5000 mm2 or less, 10000 mm2 or less, or in a range between any two of these values.

Device and Assay with High Uniformity

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm² (centimeter square) to 100 kg/cm², (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

EXAMPLES OF PRESENT INVENTION

AA1. A device for forming a thin fluidic sample layer with a uniform predetermined thickness by pressing, comprising:
a first plate, a second plate, and spacers, wherein:
i. the plates are movable relative to each other into different configurations;
ii. one or both plates are flexible;
iii. each of the plates comprises an inner surface that has a sample contact area for contacting a fluidic sample;
iv. each of the plates comprises, on its respective outer surface, a force area for applying an pressing force that forces the plates together;
v. one or both of the plates comprise the spacers that are permanently fixed on the inner surface of a respective plate;
vi. the spacers have a predetermined substantially uniform height that is equal to or less than 200 microns, and a predetermined fixed inter-spacer-distance;
vii. the fourth power of the inter-spacer-distance (ISD) divided by the thickness (h) and the Young's modulus (E) of the flexible plate (ISD$^4$/(hE)) is 5×10$^6$ um$^3$/GPa or less; and
viii. at least one of the spacers is inside the sample contact area;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration and the plates are forced to the closed configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA2. A method of forming a thin fluidic sample layer with a uniform predetermined thickness by pressing, comprising the steps of:
(a) obtaining a device of embodiment AA1;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA3. A device for analyzing a fluidic sample, comprising:
a first plate, a second plate, and spacers, wherein:
i. the plates are movable relative to each other into different configurations;
ii. one or both plates are flexible;
iii. each of the plates has, on its respective inner surface, a sample contact area for contacting a fluidic sample,
iv. one or both of the plates comprise the spacers and the spacers are fixed on the inner surface of a respective plate;
v. the spacers have a predetermined substantially uniform height that is equal to or less than 200 microns, and the inter-spacer-distance is predetermined;
vi. the Young's modulus of the spacers multiplied by the filling factor of the spacers is at least 2 MPa; and
vii. at least one of the spacers is inside the sample contact area; and
wherein one of the configurations is an open configuration, in which: the two plates are partially or completely separated apart, the spacing between the plates is not regulated by the spacers, and the sample is deposited on one or both of the plates; and wherein another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

AA4. A method of forming a thin fluidic sample layer with a uniform predetermined thickness by pressing, comprising the steps of:
(a) obtaining a device of embodiment AA3;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA5. A device for analyzing a fluidic sample, comprising:
a first plate and a second plate, wherein:
i. the plates are movable relative to each other into different configurations;
ii. one or both plates are flexible;
iii. each of the plates has, on its respective surface, a sample contact area for contacting a sample that contains an analyte,
iv. one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 um, and wherein at least one of the spacers is inside the sample contact area;
wherein one of the configurations is an open configuration, in which: the two plates are separated apart, the spacing between the plates is not regulated by the spacers, and the sample is deposited on one or both of the plates; and
wherein another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

AA6. A method of forming a thin fluidic sample layer with a uniform predetermined thickness by pressing, comprising the steps of:
(a) obtaining a device of embodiment AA5;
(b) depositing a fluidic sample on one or both of the plates; when the plates are configured in an open configuration, wherein the open configuration is a configuration in which the two plates are partially or completely separated apart and the spacing between the plates is not regulated by the spacers;
(c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

AA7. A device for forming a thin fluidic sample layer with a uniform predetermined thickness by pressing, comprising:
a first plate, a second plate, and spacers, wherein:
i. the plates are movable relative to each other into different configurations;
ii. one or both plates are flexible;
iii. each of the plates comprises, on its respective inner surface, a sample contact area for contacting and/or compressing a fluidic sample;
iv. each of the plates comprises, on its respective outer surface, an area for applying a force that forces the plates together;
v. one or both of the plates comprise the spacers that are permanently fixed on the inner surface of a respective plate;
vi. the spacers have a predetermined substantially uniform height that is equal to or less than 200 microns, a predetermined width, and a predetermined fixed inter-spacer-distance;
vii. a ratio of the inter-spacer-distance to the spacer width is 1.5 or larger; and
viii. at least one of the spacers is inside the sample contact area;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA8. A method of forming a thin fluidic sample layer with a uniform predetermined thickness by pressing with an imprecise pressing force, comprising the steps of:
(a) obtaining a device of embodiment AA7;
(b) obtaining a fluidic sample;
(c) depositing the sample on one or both of the plates; when the plates are configured in an open configuration, wherein the open configuration is a configuration in which the two plates are partially or completely separated apart and the spacing between the plates is not regulated by the spacers;
(d) after (c), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

The devices or methods of any prior embodiment, wherein the spacers have a shape of pillar with a foot fixed on one of the plates and a flat top surface for contacting the other plate.

The devices or methods of any prior embodiment, wherein the spacers have a shape of pillar with a foot fixed on one of the plates, a flat top surface for contacting the other plate, substantially uniform cross-section.

The devices or methods of any prior embodiment, wherein the spacers have a shape of pillar with a foot fixed on one of the plates and a flat top surface for contacting the other plate, wherein the flat top surface of the pillars has a variation in less than 10 nm.

The devices or methods of any prior embodiment, wherein the spacers have a shape of pillar with a foot fixed on one of the plates and a flat top surface for contacting the other plate, wherein the flat top surface of the pillars has a variation in less than 50 nm.

The devices or methods of any prior embodiment, wherein the spacers have a shape of pillar with a foot fixed on one of the plates and a flat top surface for contacting the other plate, wherein the flat top surface of the pillars has a variation in less than 50 nm.

The devices or methods of any prior embodiment, wherein the spacers have a shape of pillar with a foot fixed on one of the plates and a flat top surface for contacting the other plate, wherein the flat top surface of the pillars has a variation in less than 10 nm, 20 nm, 30 nm, 100 nm, 200 nm, or in a range of any two of the values.

The devices or methods of any prior embodiment, wherein the Young's modulus of the spacers multiplied by the filling factor of the spacers is at least 2 MPa.

The devices or methods of any prior embodiment, wherein the sample comprises an analyte and the predetermined constant inter-spacer distance is at least about 2 times larger than the size of the analyte, up to 200 um.

The devices or methods of any prior embodiment, wherein the sample comprise an analyte, the predetermined constant inter-spacer distance is at least about 2 times larger than the size of the analyte, up to 200 um, and the Young's modulus of the spacers multiplied by the filling factor of the spacers is at least 2 MPa.

The devices or methods of any prior embodiment, wherein a fourth power of the inter-spacer-distance (IDS) divided by the thickness (h) and the Young's modulus (E) of the flexible plate (ISD^4/(hE)) is 5×10^6 um^3/GPa or less.

The devices or methods of any prior embodiment, wherein a fourth power of the inter-spacer-distance (IDS) divided by the thickness (h) and the Young's modulus (E) of the flexible plate (ISD^4/(hE)) is 1×10^6 um^3/GPa or less.

The devices or methods of any prior embodiment, wherein a fourth power of the inter-spacer-distance (IDS) divided by the thickness (h) and the Young's modulus (E) of the flexible plate (ISD^4/(hE)) is 5×10^5 um^3/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD^4/(hE)) is 1×10^5 um^3/GPa or less.

The devices or methods of any prior embodiment, wherein the Young's modulus of the spacers multiplied by the filling factor of the spacers is at least 2 MPa, and a fourth power of the inter-spacer-distance (IDS) divided by the thickness (h) and the Young's modulus (E) of the flexible plate (ISD^4/(hE)) is 1×10^4 um^3/GPa or less.

The devices or methods of any prior embodiment, wherein the Young's modulus of the spacers multiplied by the filling factor of the spacers is at least 20 MPa.

The devices or methods of any prior embodiment, wherein the ratio of the inter-spacing distance of the spacers to the average width of the spacer is 2 or larger.

The devices or methods of any prior embodiment, wherein the ratio of the inter-spacing distance of the spacers to the average width of the spacer is 2 or larger, and the Young's modulus of the spacers multiplied by the filling factor of the spacers is at least 2 MPa.

The devices or methods of any prior embodiment, wherein inter-spacer distance that is at least about 2 times larger than the size of the analyte, up to 200 um.

The devices or methods of any prior embodiment, wherein a ratio of the inter-spacer-distance to the spacer width is 1.5 or larger.

The devices or methods of any prior embodiment, wherein a ratio of the width to the height of the spacer is 1 or larger.

The devices or methods of any prior embodiment, wherein a ratio of the width to the height of the spacer is 1.5 or larger.

The devices or methods of any prior embodiment, wherein a ratio of the width to the height of the spacer is 2 or larger.

The devices or methods of any prior embodiment, wherein a ratio of the width to the height of the spacer is larger than 2, 3, 5, 10, 20, 30, 50, or in a range of any two the value.

The methods of any prior embodiment, wherein the force that presses the two plates into the closed configuration is an imprecise pressing force.

The methods of any prior embodiment, wherein the force that presses the two plates into the closed configuration is an imprecise pressing force provided by human hand.

The methods of any prior embodiment, wherein the forcing of the two plates to compress at least part of the sample into a layer of substantially uniform thickness comprises a use of a conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 20% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied.

The methods of any prior embodiment, wherein the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness uniform of 20% or less.

The methods of any prior embodiment, wherein the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

The devices or methods of any prior embodiment, wherein the flexible plate has a thickness of in the range of 10 um to 200 um.

The devices or methods of any prior embodiment, wherein the flexible plate has a thickness of in the range of 20 um to 100 um.

The devices or methods of any prior embodiment, wherein the flexible plate has a thickness of in the range of 25 um to 180 um.

The devices or methods of any prior embodiment, wherein the flexible plate has a thickness of in the range of 200 um to 260 um.

The devices or methods of any prior embodiment, wherein the flexible plate has a thickness of equal to or less than 250 um, 225 um, 200 um, 175 um, 150 um, 125 um, 100 um, 75 um, 50 um, 25 um, 10 um, 5 um, 1 um, or in a range between the two of the values.

The devices or methods of any prior method, wherein the sample has a viscosity in the range of 0.1 to 4 (mPa*s).

The devices or methods of any prior embodiment, wherein the flexible plate has a thickness of in the range of 200 um to 260 um.

The devices or methods of any prior embodiment, wherein the flexible plate has a thickness in the range of 20 um to 200 um and Young's modulus in the range 0.1 to 5 GPa.

1. The method of any prior claim, wherein the sample deposition of step (b) is a deposition directly from a subject to the plate without using any transferring devices.
2. The method any prior claim, wherein during the deposition of step (b), the amount of the sample deposited on the plate is unknown.
3. The method of any prior claim, wherein the method further comprises a analyzing step (e) that analyze the sample.
4. The method of any prior claim, wherein the analyzing step (e) comprises calculating the volume of a relevant sample volume by measuring the lateral area of the relevant sample volume and calculating the volume from the lateral area and the predetermined spacer height.
5. The method of any prior claim, wherein the analyzing step (e) comprises measuring:
   i. imaging, luminescence selected from photoluminescence, electroluminescence, and electrochemiluminescence,
   iii. surface Raman scattering,
   iv. electrical impedance selected from resistance, capacitance, and inductance, or
   v. any combination of i-iv.
6. The method of any prior claim, wherein the analyzing step (e) comprises reading, image analysis, or counting of the analyte, or a combination of thereof.
7. The method of any prior claim, wherein the sample contains one or plurality of analytes, and one or both plate sample contact surfaces comprise one or a plurality of binding sites that each binds and immobilize a respective analyte.
8. The method of any prior claim, wherein one or both plate sample contact surfaces comprise one or a plurality of storage sites that each stores a reagent or reagents, wherein the reagent(s) dissolve and diffuse in the sample during or after step (c).
9. The method of any prior claim, wherein one or both plate sample contact surfaces comprises one or a plurality of amplification sites that are each capable of amplifying a signal from the analyte or a label of the analyte when the analyte or label is within 500 nm from an amplification site.
10. The method of any prior claim, wherein:
    i. one or both plate sample contact surfaces comprise one or a plurality of binding sites that each binds and immobilize a respective analyte; or
    ii. one or both plate sample contact surfaces comprise, one or a plurality of storage sites that each stores a reagent or reagents; wherein the reagent(s) dissolve and diffuse in the sample during or after step (c), and wherein the sample contains one or plurality of analytes; or
    iii. one or a plurality of amplification sites that are each capable of amplifying a signal from the analyte or a label of the analyte when the analyte or label is 500 nm from the amplification site; or
    iv. any combination of i to iii.
11. The devices or methods of any prior embodiment, wherein the liquid sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
12. The devices or methods of any prior embodiment, wherein the layer of uniform thickness in the closed configuration is less than 150 um.
13. The method of any prior claim, wherein the pressing is provided by a pressured liquid, a pressed gas, or a conformal material.
14. The method of any prior claim, wherein the analyzing comprises counting cells in the layer of uniform thickness.
15. The method of any prior claim, wherein the analyzing comprises performing an assay in the layer of uniform thickness.
16. The devices or methods of any prior embodiment, wherein the assay is a binding assay or biochemical assay.
17. The method of any prior claim, wherein the sample deposited has a total volume less 0.5 uL
18. The method of any prior claim, wherein multiple drops of sample are deposited onto one or both of the plates.
19. The devices or methods of any prior embodiment, wherein the inter-spacer distance is in the range of 1 □m to 120 □m.
20. The devices or methods of any prior embodiment, wherein the inter-spacer distance is in the range of 120 □m to 50 □m.
21. The devices or methods of any prior embodiment, wherein the inter-spacer distance is in the range of 120 □m to 200 □m.
22. The device of any prior device claim, wherein the flexible plates have a thickness in the range of 20 um to 250 um and Young's modulus in the range 0.1 to 5 GPa.
23. The device of any prior device claim, wherein for a flexible plate, the thickness of the flexible plate times the Young's modulus of the flexible plate is in the range 60 to 750 GPa-um.

24. The device of any prior device claim, wherein the layer of uniform thickness sample is uniform over a lateral area that is at least 1 mm².
25. The device of any prior device claim, wherein the layer of uniform thickness sample is uniform over a lateral area that is at least 3 mm².
26. The device of any prior device claim, wherein the layer of uniform thickness sample is uniform over a lateral area that is at least 5 mm².
27. The device of any prior device claim, wherein the layer of uniform thickness sample is uniform over a lateral area that is at least 10 mm².
28. The device of any prior device claim, wherein the layer of uniform thickness sample is uniform over a lateral area that is at least 20 mm².
29. The device of any prior device claim, wherein the layer of uniform thickness sample is uniform over a lateral area that is in a range of 20 mm² to 100 mm².
30. The device of any prior device claim, wherein the spacers are pillars with a cross-sectional shape selected from round, polygonal, circular, square, rectangular, oval, elliptical, or any combination of the same.
31. The device of any prior device claim, wherein the spacers have pillar shape, have a substantially flat top surface, and have substantially uniform cross-section, wherein, for each spacer, the ratio of the lateral dimension of the spacer to its height is at least 1.
32. The device of any prior device claim, wherein the inter spacer distance is periodic.
33. The device of any prior device claim, wherein the spacers have a filling factor of 1% or higher, wherein the filling factor is the ratio of the spacer contact area to the total plate area.
34. The device of any prior device claim, wherein the Young's modulus of the spacers times the filling factor of the spacers is equal or larger than 20 MPa, wherein the filling factor is the ratio of the spacer contact area to the total plate area.
35. The device of any prior device claim, wherein the spacing between the two plates at the closed configuration is in less 200 um.
36. The device of any prior device claim, wherein the spacing between the two plates at the closed configuration is a value selected from between 1.8 um and 3.5 um.
37. The device of any prior device claim, wherein the spacing are fixed on a plate by directly embossing the plate or injection molding of the plate.
38. The device of any prior device claim, wherein the materials of the plate and the spacers are selected from polystyrene, PMMA, PC, COC, COP, or another plastic.
39. The device of any prior device claim, wherein the spacers have a pillar shape, and the sidewall corners of the spacers have a round shape with a radius of curvature at least 1 □m.
40. The device of any prior device claim, wherein the spacers have a density of at least 1000/mm².
41. The device of any prior device claim, wherein at least one of the plates is transparent.
42. The device of any prior device claim, wherein the mold used to make the spacers is fabricated by a mold containing features that are fabricated by either (a) directly reactive ion etching or ion beam etched or (b) by a duplication or multiple duplication of the features that are reactive ion etched or ion beam etched.
43. The devices or methods of any prior embodiment, wherein the spacers are configured, such that the filling factor is in the range of 1% to 5%.

The devices or methods of any prior embodiment, wherein the surface variation is relative to the spacer height and the ratio of the pillar flat top surface variation to the spacer height is less than 0.5%, 1%, 3%,5%,7%,10%,15%, 20%, 30%,40%, or in a range between any two of the values. A preferred flat pillar top smoothness has a ratio of the pillar flat top surface variation to the spacer height is less than 2%, 5%, or 10%.
44. The devices or methods of any prior embodiment, wherein the spacers are configured, such that the filling factor is in the range of 1% to 5%.
45. The devices or methods of any prior embodiment, wherein the spacers are configured, such that the filling factor is in the range of 5% to 10%.
46. The devices or methods of any prior embodiment, wherein the spacers are configured, such that the filling factor is in the range of 10% to 20%.
47. The devices or methods of any prior embodiment, wherein the spacers are configured, such that the filling factor is in the range of 20% to 30%.
48. The devices or methods of any prior embodiment, wherein the spacers are configured, such that the filling factor is 5%, 10%, 20%, 30%, 40%, 50%, or in a range of any two of the values.
49. The devices or methods of any prior embodiment, wherein the spacers are configured, such that the filling factor is 50%, 60%, 70%, 80%, or in a range of any two of the values.
50. The devices or methods of any prior embodiment, wherein the spacers are configured, such that the filling factor multiplies the Young's modulus of the spacer is in the range of 2 MPa and 10 MPa.
51. The devices or methods of any prior embodiment, wherein the spacers are configured, such that the filling factor multiplies the Young's modulus of the spacer is in the range of 10 MPa and 20 MPa.
52. The devices or methods of any prior embodiment, wherein the spacers are configured, such that the filling factor multiplies the Young's modulus of the spacer is in the range of 20 MPa and 40 MPa.
53. The devices or methods of any prior embodiment, wherein the spacers are configured, such that the filling factor multiplies the Young's modulus of the spacer is in the range of 40 MPa and 80 MPa.
54. The devices or methods of any prior embodiment, wherein the spacers are configured, such that the filling factor multiplies the Young's modulus of the spacer is in the range of 80 MPa and 120 MPa.
55. The devices or methods of any prior embodiment, wherein the spacers are configured, such that the filling factor multiplies the Young's modulus of the spacer is in the range of 120 MPa to 150 MPa.
56. The devices or methods of any prior embodiment, wherein the device further comprises a dry reagent coated on one or both plates.
57. The devices or methods of any prior embodiment, wherein the device further comprises, on one or both plates, a dry binding site that has a predetermined area, wherein the dry binding site binds to and immobilizes an analyte in the sample.
58. The devices or methods of any prior embodiment, wherein the device further comprises, on one or both plates, a releasable dry reagent and a release time control material that delays the time that the releasable dry regent is released into the sample.

59. The device of any prior embodiment, wherein the release time control material delays the time that the dry regent starts is released into the sample by at least 3 seconds.
60. The device of any prior embodiment, wherein the regent comprises anticoagulant and/or staining reagent(s)
61. The device of any prior embodiment, wherein the reagent comprises cell lysing reagent(s)
62. The devices or methods of any prior embodiment, wherein the device further comprises, on one or both plates, one or a plurality of dry binding sites and/or one or a plurality of reagent sites.
63. The device of any prior device embodiment, wherein the analyte comprises a molecule (e.g., a protein, peptides, DNA, RNA, nucleic acid, or other molecule), cells, tissues, viruses, and nanoparticles with different shapes.
64. The device of any prior device embodiment, wherein the analyte comprises white blood cells, red blood cells and platelets.
65. The device of any prior device embodiment, wherein the analyte is stained.
66. The devices or methods of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.
67. The devices or methods of any prior embodiment, wherein for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.
68. The devices or methods of any prior embodiment, wherein for a flexible plate, the thickness of the flexible plate times the Young's modulus of the flexible plate is in the range 60 to 750 GPa-um.
69. The devices or methods of any prior embodiment, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3/GPa$,
70. The devices or methods of any prior embodiment, wherein one or both plates comprise a location marker, either on a surface of or inside the plate, that provide information of a location of the plate.
71. The devices or methods of any prior embodiment, wherein one or both plates comprise a scale marker, either on a surface of or inside the plate, that provide information of a lateral dimension of a structure of the sample and/or the plate.
72. The devices or methods of any prior embodiment, wherein one or both plates comprise an imaging marker, either on surface of or inside the plate, that assists an imaging of the sample.
73. The devices or methods of any prior embodiment, wherein the spacers functions as a location marker, a scale marker, an imaging marker, or any combination of thereof.
74. The devices or methods of any prior embodiment, wherein the average thickness of the layer of uniform thickness is about equal to a minimum dimension of an analyte in the sample.
75. The devices or methods of any prior embodiment, wherein the inter-spacer distance is in the range of 7 um to 50 um.
76. The devices or methods of any prior embodiment, wherein the inter-spacer distance is in the range of 50 um to 120 um.
77. The devices or methods of any prior embodiment, wherein the inter-spacer distance is in the range of 120 um to 200 um.
78. The devices or methods of any prior embodiment, wherein the inter-spacer distance is substantially periodic.
79. The devices or methods of any prior embodiment, wherein the spacers are pillars with a cross-sectional shape selected from round, polygonal, circular, square, rectangular, oval, elliptical, or any combination of the same.
80. The devices or methods of any prior embodiment, wherein the spacers have are pillar shape and have a substantially flat top surface, wherein, for each spacer, the ratio of the lateral dimension of the spacer to its height is at least 1.
81. The devices or methods of any prior embodiment, wherein each spacer has the ratio of the lateral dimension of the spacer to its height is at least 1.
82. The devices or methods of any prior embodiment, wherein the minimum lateral dimension of spacer is less than or substantially equal to the minimum dimension of an analyte in the sample.
83. The devices or methods of any prior embodiment, wherein the minimum lateral dimension of spacer is in the range of 0.5 um to 100 um.
84. The devices or methods of any prior embodiment, wherein the minimum lateral dimension of spacer is in the range of 0.5 um to 10 um.
85. The devices or methods of any prior embodiment, wherein the sample is blood.
86. The devices or methods of any prior embodiment, wherein the sample is whole blood without dilution by liquid.
87. The devices or methods of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
88. The devices or methods of any prior embodiment, wherein the sample is a biological sample, an environmental sample, a chemical sample, or clinical sample.
89. The devices or methods of any prior embodiment, wherein the spacers have a pillar shape, and the sidewall corners of the spacers have a round shape with a radius of curvature at least 1 um.
90. The devices or methods of any prior embodiment, wherein the spacers have a density of at least $100/mm^2$.
91. The devices or methods of any prior embodiment, wherein the spacers have a density of at least $1000/mm^2$.
92. The devices or methods of any prior embodiment, wherein at least one of the plates is transparent.
93. The devices or methods of any prior embodiment, wherein at least one of the plates is made from a flexible polymer.
94. The devices or methods of any prior embodiment, wherein, for a pressure that compresses the plates, the spacers are not compressible and/or, independently, only one of the plates is flexible.

95. The device of any of any prior embodiment, wherein the flexible plate has a thickness in the range of 10 um to 200 um.
96. The devices or methods of any prior embodiment, wherein the variation is less than 30%.
97. The devices or methods of any prior embodiment, wherein the variation is less than 10%.
98. The devices or methods of any prior embodiment, wherein the variation is less than 5%.
99. The devices or methods of any prior embodiment, wherein the first and second plates are connected and are configured to be changed from the open configuration to the closed configuration by folding the plates.
100. The devices or methods of any prior embodiment, wherein the first and second plates are connected by a hinge and are configured to be changed from the open configuration to the closed configuration by folding the plates along the hinge.
101. The devices or methods of any prior embodiment, wherein the first and second plates are connected by a hinge that is a separate material to the plates, and are configured to be changed from the open configuration to the closed configuration by folding the plates along the hinge
102. The devices or methods of any prior embodiment, wherein the first and second plates are made in a single piece of material and are configured to be changed from the open configuration to the closed configuration by folding the plates.
103. The devices or methods of any prior embodiment, wherein the layer of uniform thickness sample is uniform over a lateral area that is at least 1 mm$^2$.
104. The devices or methods of any prior embodiment, wherein the device is configured to analyze the sample in 60 seconds or less.
105. The devices or methods of any prior embodiment, wherein at the closed configuration, the final sample thickness device is configured to analyze the sample in 60 seconds or less.
106. The devices or methods of any prior embodiment, wherein at the closed configuration, the final sample thickness device is configured to analyze the sample in 10 seconds or less.
107. The devices or methods of any prior embodiment, wherein the dry binding site comprises a capture agent.
108. The devices or methods of any prior embodiment, wherein the dry binding site comprises an antibody or nucleic acid.
109. The devices or methods of any prior embodiment, wherein the releasable dry reagent is a labeled reagent.
110. The devices or methods of any prior embodiment, wherein the releasable dry reagent is a fluorescently-labeled reagent.
111. The devices or methods of any prior embodiment, wherein the releasable dry reagent is a fluorescently-labeled antibody.
112. The devices or methods of any prior embodiment, wherein the releasable dry reagent is a cell stain.
113. The devices or methods of any prior embodiment, wherein the releasable dry reagent is a cell lysing.
114. The devices or methods of any prior embodiment, wherein the detector is an optical detector that detects an optical signal.
115. The devices or methods of any prior embodiment, wherein the detector is an electric detector that detect electrical signal.
116. The device of any prior device embodiment, wherein the spacing are fixed on a plate by directly embossing the plate or injection molding of the plate.
117. The device of any prior device embodiment, wherein the materials of the plate and the spacers are selected from polystyrene, PMMA, PC, COC, COP, or another plastic.
118. A system for rapidly analyzing a sample using a mobile phone comprising:
    (a) a device of any prior embodiment;
    (b) a mobile communication device comprising:
        i. one or a plurality of cameras for the detecting and/or imaging the sample;
        ii. electronics, signal processors, hardware and software for receiving and/or processing the detected signal and/or the image of the sample and for remote communication; and
    (c) a light source from either the mobile communication device or an external source;
    wherein the detector in the devices or methods of any prior embodiment is provided by the mobile communication device, and detects an analyte in the sample at the closed configuration.
119. The system of any prior system embodiment, wherein one of the plates has a binding site that binds an analyte, wherein at least part of the uniform sample thickness layer is over the binding site, and is substantially less than the average lateral linear dimension of the binding site.
120. The system of any prior system embodiment, further comprising:
    (d) a housing configured to hold the sample and to be mounted to the mobile communication device.
121. The system of any prior system embodiment, wherein the housing comprises optics for facilitating the imaging and/or signal processing of the sample by the mobile communication device, and a mount configured to hold the optics on the mobile communication device.
122. The system of any prior system embodiment, wherein an element of the optics in the housing is movable relative to the housing.
123. The system of any prior system embodiment, wherein the mobile communication device is configured to communicate test results to a medical professional, a medical facility or an insurance company.
124. The system of any prior system embodiment, wherein the mobile communication device is further configured to communicate information on the test and the subject with the medical professional, medical facility or insurance company.
125. The system of any prior system embodiment, wherein the mobile communication device is further configured to communicate information of the test to a cloud network, and the cloud network process the information to refine the test results.
126. The system of any prior system embodiment, wherein the mobile communication device is further configured to communicate information of the test and the subject to a cloud network, the cloud network process the information to refine the test results, and the refined test results will send back the subject.
127. The system of any prior system embodiment, wherein the mobile communication device is configured to receive a prescription, diagnosis or a recommendation from a medical professional.
128. The system of any prior system embodiment, wherein the mobile communication device is configured with hardware and software to:

(a) capture an image of the sample;
(b) analyze a test location and a control location in in image; and
(c) compare a value obtained from analysis of the test location to a threshold value that characterizes the rapid diagnostic test.

129. The system of any prior system embodiment, wherein at least one of the plates comprises a storage site in which assay reagents are stored.

130. The system of any prior system embodiment, at least one of the cameras reads a signal from the device.

131. The system of any prior system embodiment, wherein the mobile communication device communicates with the remote location via a WIFI or cellular network.

132. The system of any prior system embodiment, wherein the mobile communication device is a mobile phone.

133. A method for rapidly analyzing an analyte in a sample using a mobile phone, comprising:
(a) depositing a sample on the device of any prior system embodiment;
(b) assaying an analyte in the sample deposited on the device to generate a result; and
(c) communicating the result from the mobile communication device to a location remote from the mobile communication device.

134. The method of any prior embodiments, wherein the analyte comprises a molecule (e.g., a protein, peptides, DNA, RNA, nucleic acid, or other molecule), cells, tissues, viruses, and nanoparticles with different shapes.

135. The method of any prior embodiment, wherein the analyte comprises white blood cell, red blood cell and platelets.

136. The method of any prior embodiment, wherein the assaying comprises performing a white blood cells differential assay.

137. The method of any prior embodiments, wherein the method comprises:
analyzing the results at the remote location to provide an analyzed result; and
communicating the analyzed result from the remote location to the mobile communication device.

138. The method of any prior embodiment, wherein the analysis is done by a medical professional at a remote location.

139. The method of any prior embodiment, wherein the mobile communication device receives a prescription, diagnosis or a recommendation from a medical professional at a remote location.

140. The method of any prior embodiment, wherein the sample is a bodily fluid.

141. The method of any prior embodiment, wherein the bodily fluid is blood, saliva or urine.

142. The method of any prior embodiment, wherein the sample is whole blood without dilution by a liquid.

143. The method of any prior embodiment, wherein the assaying step comprises detecting an analyte in the sample.

144. The method of any prior embodiment, wherein the analyte is a biomarker.

145. The method of any prior embodiment, wherein the analyte is a protein, nucleic acid, cell, or metabolite.

146. The method of any prior embodiment, wherein the method comprises counting the number of red blood cells.

147. The method of any of any prior embodiment, wherein the method comprises counting the number of white blood cells.

148. The method of any prior embodiment, wherein method comprises staining the cells in the sample and counting the number of neutrophils, lymphocytes, monocytes, eosinophils and basophils.

149. The method of any prior embodiments embodiment, wherein the assay done in step (b) is a binding assay or a biochemical assay.

150. A method for analyzing a sample comprising:
obtaining a device of any prior device embodiment;
depositing the sample onto one or both pates of the device;
placing the plates in a closed configuration and applying an external force over at least part of the plates; and
analyzing the layer of uniform thickness while the plates are the closed configuration.

151. The devices or methods of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

152. The devices or methods of any prior embodiment, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

153. The devices or methods of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

154. The devices or methods of any prior embodiment, wherein the analyte assay area is between a pair of electrodes.

155. The devices or methods of any prior embodiment, wherein the assay area is defined by a patch of dried reagent.

156. The devices or methods of any prior embodiment, wherein the assay area binds to and immobilizes the analyte 157. The devices or methods of any prior embodiment, wherein the assay area is defined by a patch of binding reagent that, upon contacting the sample, dissolves into the sample, diffuses in the sample, and binds to the analyte.

158. The devices or methods of any prior embodiment, wherein the inter-spacer distance is in the range of 14 □m to 200 □m.

159. The devices or methods of any prior embodiment, wherein the inter-spacer distance is in the range of 7 □m to 20 □m.

160. The devices or methods of any prior embodiment, wherein the spacers are pillars with a cross-sectional shape selected from round, polygonal, circular, square, rectangular, oval, elliptical, or any combination of the same.

161. The devices or methods of any prior embodiment, wherein the spacers have are pillar shape and have a substantially flat top surface, wherein, for each spacer, the ratio of the lateral dimension of the spacer to its height is at least 1.

162. The devices or methods of any prior embodiment, wherein the spacers have a pillar shape, and the sidewall corners of the spacers have a round shape with a radius of curvature at least 1 □m.

163. The devices or methods of any prior embodiment, wherein the spacers have a density of at least 1000/mm².

164. The devices or methods of any prior embodiment, wherein at least one of the plates is transparent.

165. The devices or methods of any prior embodiment, wherein at least one of the plates is made from a flexible polymer.

166. The devices or methods of any prior embodiment, wherein only one of the plates is flexible.

The device of any prior embodiment, wherein the area-determination device is a camera.

The area-determination device comprises an area in the sample contact area of a plate, wherein the area is less than 1/100, 1/20, 1/10, 1/6, 1/5, 1/4, 1/3, 1/2, 2/3 of the sample contact area, or in a range between any of the two values.

The area-determination device comprises a camera and an area in the sample contact area of a plate, wherein the area is in contact with the sample.

The devices or methods of any prior embodiment, wherein the deformable sample comprises a liquid sample.

The devices or methods of any prior embodiment, wherein the imprecision force has a variation at least 30% of the total force that actually is applied.

The devices or methods of any prior embodiment, wherein the imprecision force has a variation at least 20%, 30%, 40%, 50%, 60, 70%, 80%, 90% 100%, 150%, 200%, 300%, 500%, or in a range of any two values, of the total force that actually is applied.

167. The device of any prior embodiment, wherein spacers have a flat top.

168. The device of any prior embodiment, wherein the device is further configured to have, after the pressing force is removed, a sample thickness that is substantially the same in thickness and uniformity as that when the force is applied.

169. The device of any prior embodiment, wherein the imprecise force is provided by human hand.

170. The device of any prior embodiment, wherein the inter spacer distance is substantially constant.

171. The device of any prior embodiment, wherein the inter spacer distance is substantially periodic in the area of the uniform sample thickness area.

172. The device of any prior embodiment, wherein the multiplication product of the filling factor and the Young's modulus of the spacer is 2 MPa or larger.

173. The device of any prior embodiment, wherein the force is applied by hand directly or indirectly.

174. The device of any prior embodiment, wherein the force applied is in the range of 1 N to 20 N.

175. The device of any prior embodiment, wherein the force applied is in the range of 20 N to 200 N 176. The device of any prior embodiment wherein the highly uniform layer has a thickness that varies by less than 15%, 10%, or 5% of an average thickness.

177. The device of any prior embodiment, wherein the imprecise force is applied by pinching the device between a thumb and forefinger.

178. The device of any prior embodiment, wherein the predetermined sample thickness is larger than the spacer height.

179. The device of any prior embodiment, wherein the device holds itself in the closed configuration after the pressing force has been removed.

180. The device of any prior embodiment, wherein the uniform thickness sample layer area is larger than that area upon which the pressing force is applied.

181. The device of any prior embodiment, wherein the spacers do not significantly deform during application of the pressing force.

182. The device of any prior embodiment, wherein the pressing force is not predetermined beforehand and is not measured.

183. In some embodiments, the fluidic sample is replaced by a deformable sample and the embodiments for making at least a part of the fluidic sample into a uniform thickness layer can make at least a part of the deformable sample into a uniform thickness layer.

184. The devices and methods of any prior device claim, wherein the inter spacer distance is periodic.

185. The devices and methods of any prior device claim, wherein the spacers have a flat top.

186. The devices and methods of any prior device claim, wherein the inter spacer distance is at least two times large than the size of the targeted analyte in the sample.

Manufacturing of Q-Card

MA1. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) a sample overflow dam that surrounds the sample contact area is configured to present a sample flow outside of the dam;
  ii. the second plate is 10 um to 250 um thick and comprises, on its inner surface, (a) a sample contact area for contacting a sample, and (b) spacers on the sample contact area;
  iii. the hinge that connect the first and the second plates; and
wherein the first and second plate are movable relative to each other around the axis of the hinge.

MA2. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, (b) a sample overflow dam that surrounds the sample contact area is configured to present a sample flow outside of the dam, and (c) spacers on the sample contact area;
  ii. the second plate, that is 10 um to 250 um thick, comprises, on its inner surface, a sample contact area for contacting a sample;
  iii. the hinge that connect the first and the second plates; and
wherein the first and second plate are movable relative to each other around the axis of the hinge.

MA3. An embodiment of the Q-Card comprising: a first plate, a second plate, and a hinge, wherein
  i. the first plate, that is about 200 nm to 1500 nm thick, comprises, on its inner surface, (a) a sample contact area for contacting a sample, and (b) spacers on the sample contact area;

ii. the second plate, that is 10 um to 250 um thick, comprises, on its inner surface, (a) a sample contact area for contacting a sample, and (b) a sample overflow dam that surrounds the sample contact area is configured to present a sample flow outside of the dam, and;

iii. the hinge that connect the first and the second plates; and wherein the first and second plate are movable relative to each other around the axis of the hinge.

MA4 An embodiment of the Q-Card comprising: a first plate, a second plate, and a hinge, wherein i. the first plate, that is about 200 nm to 1500 nm thick, comprises, on its inner surface, a sample contact area for contacting a sample;

ii. the second plate, that is 10 um to 250 um thick, comprises, on its inner surface, (a) a sample contact area for contacting a sample, (b) a sample overflow dam that surrounds the sample contact area is configured to present a sample flow outside of the dam, and (c) spacers on the sample contact area; and iii. the hinge that connect the first and the second plates; and wherein the first and second plate are movable relative to each other around the axis of the hinge.

M1 An embodiment of a method for fabricating the Q-Card of any embodiments of MA1 to MA4, comprising:

(a) injection molding of the first plate, (b) nanoimprinting or extrusion printing of the second plate.

M2 An embodiment of a method for fabricating the Q-Card of any embodiments of MA1 to MA4, comprising:

(a) Laser cutting the first plate, (b) nanoimprinting or extrusion printing of the second plate.

M3 An embodiment of a method for fabricating the Q-Card of any embodiments of MA1 to MA4, comprising:

(a) Injection molding and laser cutting the first plate, (b) nanoimprinting or extrusion printing of the second plate.

M4 An embodiment of a method for fabricating the Q-Card of any embodiments of MA1 to MA4, comprising: nanoimprinting or extrusion printing to fabricated both the first and the second plate.

M5 An embodiment of a method for fabricating the Q-Card of any embodiments of MA1 to MA4, comprising: fabricating the first plate or the second plate, using injection molding, laser cutting the first plate, nanoimprinting, extrusion printing, or a combination of thereof.

The method of any embodiments of M1-M5, wherein the method further comprises a step of attach the hinge on the first and the second plates after the fabrication of the first and second plates.

ADDITIONAL EXAMPLES

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices/apparatus, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (µL, also "uL" herein) or less, 500 µL or less, 300 µL or less, 250 µL or less, 200 µL or less, 170 µL or less, 150 µL or less, 125 µL or less, 100 µL or less, 75 µL or less, 50 µL or less, 25 µL or less, 20 µL or less, 15 µL or less, 10 µL or less, 5 µL or less, 3 µL or less, 1 µL or less, 0.5 µL or less, 0.1 µL or less, 0.05 µL or less, 0.001 µL or less, 0.0005 µL or less, 0.0001 µL or less, 10 pL or less, 1 pL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed:

plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyimide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in U.S. Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb.8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456,631, 62/456,522, 62/456,598, 62/456,603, and 62/456,628, which were filed on Feb. 8, 2017, U.S. Provisional Application No. 62/459, 276, 62/456,904, 62/457,075, and 62/457,009, which were filed on Feb. 9, 2017, and U.S. Provisional Application No. 62/459,303, 62/459,337, and 62/459,598, which were filed on Feb. 15, 2017, and U.S. Provisional Application No. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino--fluorescein (DTAF), 2',7'dimethoxy-4'5'-dichloro-6-carboxyfluorescein (JOE), fluorescein, fluorescein isothiocyanate, QFITC, (XRITC); fluorescamine; 1R144; 1R1446; Malachite Green isothiocyanate; 4-methylumbelli-feroneortho cresol phthalein; nitrotyrosine; pararosaniline; Phenol Red; B-phycoerythrin; o-phthaldialdehyde; pyrene and derivatives: pyrene, pyrene butyrate, succinimidyl 1-pyrene); butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as Renilla reniformis, Renilla mulleri, or Ptilosarcus guernyi; "humanized" recombinant GFP (hrGFP); any of a variety of fluorescent and colored proteins from Anthozoan species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/U S2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234, 538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

What is claimed is:

1. A trackable device for sample analysis, comprising:
a first plate, a second plate, a camera, and a tracking label, wherein:
i. the plates are movable relative to each other into different configurations; and
ii. each of the plates comprises an inner surface that has a sample contact area for contacting a sample;
iii. an imager configured to image the tracking label to obtain images; and
iv. a non-transitory storage medium that stores an algorithm configured to analyze the images by artificial intelligence or machine learning;
wherein one of the configurations is an open configuration, in which the two plates are separated apart, and the sample is deposited on one or both of the plates;
wherein another configuration is a closed configuration, which is configured after the sample is deposited on one or both the plates in the open configuration;
wherein in the closed configuration at least part of the sample is compressed by the two plates into a layer of uniform thickness and is substantially stagnant relative to the plates, thereby allowing the sample in the layer to be imaged by a detecting apparatus that comprises a camera; and
wherein the tracking label is on at least one of the plates and is configured to be readable by the detecting apparatus to provide information related to the device.

2. A method of tracking a device for sample analysis, comprising:
(a) obtaining the device of claim 1;
(b) moving the plates into the closed configuration to form a card;
(c) inserting the card into a card slot, which is part of an adapter that is configured to attach to the detecting apparatus and position the plates in front of the camera;
(d) capturing at least one image of at least part of the tracking label with the camera; and
(e) extracting information related to the device based on the image.

3. The method of claim 2, wherein step (d) is conducted during step (c) and before the card reaches the locked position.

4. The method of claim 2, further comprising the step of:
(f) identifying the tracking label during the inserting of the card into the slot, or during a removal of the card from the slot, or both.

5. A method of identifying a tracking label, comprising the steps of:
(a) obtaining the device of claim 1;
(b) imaging the tracking label to obtain images; and
(c) analyzing the images by artificial intelligence or machine learning.

6. The device of claim 1, wherein the tracking label is a 1-D barcode, a 2-D barcode, a 3-D barcode, a watermark, a waveform, a machine readable medium, an image showing a string of words or numbers configured to be recognized by optional character recognition (OCR), a pattern showing a string of words or numbers configured to be recognized by optional character recognition (OCR), or a periodic pattern.

7. The device of claim 1, wherein the tracking label is positioned in an inserting area on the card, wherein the inserting area is an area on the card, from a top view, that is in front of the field of view (FoV) and can be viewed through the camera and of which images can be captured if the camera is turned on during the inserting process, or is positioned in an overshoot area on the card, wherein the overshoot area is an area on the card, from a top view, that is on the back of the field of view (FoV) and can be viewed through the camera and of which images can be captured if the camera is turned on during the inserting process, or is positioned in the same area as the field of view (FOV), or is positioned between the first plate and the second plate, or is positioned on the inner surface of the first plate, or is positioned on the outer surface of the first plate, or is positioned on the inner surface of the second plate, or is positioned on the outer surface of the second plate.

8. The device of claim 1, wherein the information comprises a unique identifier of the device, or comprises information regarding assays that can be conducted with the device, including assay type, assay processes, assay reagent, or assay troubleshooting, or comprises information regarding manufacturing of the device, including manufacturing site, manufacturing date, manufacturing process, manufacturing lot, or related personnel, or comprises information regarding warranties associated with the device.

9. The device of claim 1, wherein the tracking label is produced by printing with ink, or is produced by engraving with light (e.g. laser), or is produced by a charged beam (electron or ion), or is produced by a nanoparticle beam, or is produced by etching, or is produced by deposition of materials.

10. The device of claim 3, further comprising spacers affixed on one or both of the plates, and wherein at least part of the spacers is used as the tracking label.

11. The method of claim 10, further comprising a step of analyzing the images by artificial intelligence or machine learning.

12. A trackable device for sample analysis, comprising:
a sample card, a tracking label, a camera, and a slider, wherein:
i. the sample card comprises two plates that are configured to compress a liquid sample into a layer of uniform thickness;
ii. the tracking label is positioned on the sample card and configured to be machine-readable by a camera and provide information related to the sample card;
iii. the slider is configured to hold the sample card when the liquid sample is compressed and slide the sample card into a position in front of the camera, and
iv. a camera that images the tracking label.

13. The device of claim 12, wherein the camera captures the image of the tracking label as the card slides passes the camera.

14. A method of tracking a device for sample analysis, comprising:
(a) obtaining the device of claim 12;
(b) moving the plates into the closed configuration to form a card;
(c) sliding the card into a card slot, which is part of an adapter that is configured to position the plates in front of the camera;
(d) capturing at least one image of at least part of the tracking label with the camera; and
(e) extracting information related to the device based on the image.

15. The method of claim 14 wherein step (d) is conducted during step (c) and before the card reaches the locked position.

16. The device of claim 12, wherein the tracking label is imaged by different imagers.

17. The device of claim 12, wherein the information comprises a unique identifier of the device, or comprises information regarding assays that can be conducted with the device, including assay type, assay processes, assay reagent, or assay troubleshooting, or comprises information regarding manufacturing of the device, including manufacturing site, manufacturing date, manufacturing process, manufacturing lot, or related personnel, or comprises information regarding warranties associated with the device.

18. The device of claim 12, wherein the tracking label is produced by printing with ink, or is produced by engraving with light (e.g. laser), or is produced by a charged beam (electron or ion), or is produced by a nanoparticle beam, or is produced by etching, or is produced by deposition of materials.

19. The device of claim 12, further comprising spacers affixed on one or both of the plates, wherein at least part of the spacers is used as the tracking label.

20. A method of identifying a tracking label, comprising the steps of:
(a) obtaining the device of claim 12;
(b) compressing a sample by the sample card into a layer of uniform thickness;
(c) sliding the sample card into the front of the camera; and
(d) imaging the tracking label to obtain images.

* * * * *